(12) United States Patent  
Gisselberg et al.

(10) Patent No.: US 7,535,363 B2  
(45) Date of Patent: May 19, 2009

(54) MINIATURE RESONATING MARKER ASSEMBLY

(75) Inventors: Margo Gisselberg, Lynnwood, WA (US); Eric Hadford, Snohomish, WA (US); Steven C. Dimmer, Bellevue, WA (US); Jack Goldberg, San Diego, CA (US); Jeff Pelton, San Diego, CA (US); Kurt Zublin, Poway, CA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 26 days.

(21) Appl. No.: 11/599,244

(22) Filed: Nov. 13, 2006

(65) Prior Publication Data

US 2007/0057794 A1    Mar. 15, 2007

Related U.S. Application Data

(62) Division of application No. 09/954,700, filed on Sep. 14, 2001, now Pat. No. 7,135,978.

(51) Int. Cl.  
G08B 13/14 (2006.01)

(52) U.S. Cl. .................. 340/572.5; 340/572.7; 343/750

(58) Field of Classification Search ... 340/572.1–572.9, 340/10.1  
See application file for complete search history.

(56) References Cited

U.S. PATENT DOCUMENTS

| 3,545,078 | A | * | 12/1970 | Lightner | 29/605 |
|---|---|---|---|---|---|
| 3,577,160 | A | | 5/1971 | White | |
| 3,752,960 | A | | 8/1973 | Walton | |
| 3,836,842 | A | | 9/1974 | Zimmermann et al. | |
| 3,967,161 | A | | 6/1976 | Lichtblau | |
| 3,969,629 | A | | 7/1976 | McIntyre | |
| 4,017,858 | A | | 4/1977 | Kuipers | |
| 4,023,167 | A | | 5/1977 | Wahlstrom | |
| 4,065,753 | A | | 12/1977 | Paul, Jr. | |

(Continued)

FOREIGN PATENT DOCUMENTS

DE    19914455    10/2000

(Continued)

OTHER PUBLICATIONS

U.S. Appl. No. 10/416,827, David Krag.

(Continued)

*Primary Examiner*—George A Bugg  
(74) *Attorney, Agent, or Firm*—Perkins Coie LLP

(57) ABSTRACT

A miniature resonating marker assembly that includes, in one embodiment, a ferromagnetic core, a wire coil disposed around the core, and a capacitor connected to the wire coil adjacent to the magnetic core. The core, coil, and capacitor form a signal element that, when energized, generates a magnetic field at a selected resonant frequency. The magnetic field has a magnetic center point positioned along at least one axis of the signal element. An inert encapsulation member encapsulates the signal element therein and defines a geometric shape of the resonating marker assembly. The geometric shape has a geometric center point substantially coincident with the magnetic center point along at least a first axis of the signal element. The shape and configuration of the assembly also provides for a miniature signal element specifically tuned to resonate at a selected frequency with a high quality factor.

12 Claims, 9 Drawing Sheets

U.S. PATENT DOCUMENTS

| | | | |
|---|---|---|---|
| 4,087,791 A | 5/1978 | Lemberger |
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson et al. |
| 4,230,123 A | 10/1980 | Hawkins |
| 4,260,990 A | 4/1981 | Lichtblau |
| 4,393,872 A | 7/1983 | Reznik et al. |
| 4,395,910 A | 8/1983 | Thomenius |
| 4,466,075 A | 8/1984 | Groch |
| 4,618,822 A | 10/1986 | Hansen |
| 4,618,978 A | 10/1986 | Cosman |
| 4,633,250 A | 12/1986 | Anderson |
| 4,642,786 A | 2/1987 | Hansen |
| 4,643,196 A | 2/1987 | Tanaka et al. |
| 4,696,287 A | 9/1987 | Hortmann et al. |
| 4,737,794 A | 4/1988 | Jones |
| 4,795,995 A | 1/1989 | Eccleston |
| 4,799,495 A | 1/1989 | Hawkins |
| 4,832,055 A | 5/1989 | Palestrant |
| 4,849,692 A | 7/1989 | Blood |
| 4,909,789 A | 3/1990 | Taguchi et al. |
| 4,936,823 A | 6/1990 | Colvin et al. |
| 4,945,305 A | 7/1990 | Blood |
| 4,992,794 A | 2/1991 | Brouwers |
| 4,994,079 A | 2/1991 | Genese |
| 5,019,713 A | 5/1991 | Schmidt et al. |
| 5,031,634 A | 7/1991 | Simon |
| 5,050,608 A | 9/1991 | Watanabe et al. |
| 5,062,847 A | 11/1991 | Barnes |
| 5,095,224 A | 3/1992 | Renger |
| 5,099,845 A | 3/1992 | Besz et al. |
| 5,107,862 A | 4/1992 | Fabian |
| 5,142,292 A | 8/1992 | Chang |
| 5,170,055 A | 12/1992 | Carroll |
| 5,188,368 A | 2/1993 | Ryan |
| 5,189,690 A | 2/1993 | Samuel |
| 5,197,466 A | 3/1993 | Marchosky |
| 5,198,877 A | 3/1993 | Schulz |
| 5,205,289 A | 4/1993 | Hardy |
| 5,211,129 A | 5/1993 | Taylor |
| 5,211,164 A | 5/1993 | Allen |
| 5,221,269 A | 6/1993 | Miller |
| 5,223,851 A | 6/1993 | Hadden |
| 5,230,338 A | 7/1993 | Allen |
| 5,233,990 A | 8/1993 | Barnea |
| 5,240,011 A | 8/1993 | Assa |
| 5,246,005 A | 9/1993 | Carroll |
| 5,262,772 A | 11/1993 | Urbas |
| 5,285,772 A | 2/1994 | Rattner et al. |
| 5,325,873 A | 7/1994 | Hirschi |
| 5,377,678 A | 1/1995 | Dumoulin |
| 5,386,191 A | 1/1995 | McCarten et al. |
| 5,396,889 A | 3/1995 | Ueda et al. |
| 5,396,905 A | 3/1995 | Newman et al. |
| 5,397,329 A | 3/1995 | Allen |
| 5,400,787 A | 3/1995 | Marandos |
| 5,411,026 A | 5/1995 | Carol |
| 5,417,210 A | 5/1995 | Funda |
| 5,423,334 A | 6/1995 | Jordan |
| 5,425,367 A | 6/1995 | Shapiro |
| 5,425,382 A | 6/1995 | Golden et al. |
| 5,446,548 A | 8/1995 | Gerig |
| 5,453,686 A | 9/1995 | Anderson |
| 5,509,900 A | 4/1996 | Kirkman |
| 5,515,853 A | 5/1996 | Smith |
| 5,526,812 A | 6/1996 | Dumoulin |
| 5,528,651 A | 6/1996 | Leksell |
| 5,546,951 A | 8/1996 | Ben-Haim |
| 5,558,091 A | 9/1996 | Acker |
| 5,559,435 A | 9/1996 | Harada et al. |
| 5,568,809 A | 10/1996 | Ben-Haim |
| 5,572,999 A | 11/1996 | Funda |
| 5,617,857 A | 4/1997 | Chader |
| 5,621,779 A | 4/1997 | Hughes et al. |
| 5,622,170 A | 4/1997 | Schulz |
| 5,622,187 A | 4/1997 | Carol |
| 5,629,967 A | 5/1997 | Leksell |
| 5,630,431 A | 5/1997 | Taylor |
| 5,638,819 A | 6/1997 | Manwaring et al. |
| 5,645,065 A | 7/1997 | Shapiro |
| 5,680,106 A | 10/1997 | Schrott |
| 5,681,326 A | 10/1997 | Lax |
| 5,697,384 A | 12/1997 | Miyawaki |
| 5,707,362 A | 1/1998 | Yoon |
| 5,707,390 A | 1/1998 | Bonutti |
| 5,724,030 A | 3/1998 | Urbas |
| 5,727,552 A | 3/1998 | Ryan |
| 5,735,795 A | 4/1998 | Young et al. |
| 5,745,545 A | 4/1998 | Hughes |
| RE35,816 E | 6/1998 | Schulz |
| 5,764,052 A | 6/1998 | Renger |
| 5,769,861 A | 6/1998 | Vilsmeier |
| 5,779,638 A | 7/1998 | Vesely |
| 5,782,775 A | 7/1998 | Milliman |
| 5,797,849 A | 8/1998 | Vesely |
| 5,805,661 A | 9/1998 | Leksell |
| 5,810,851 A | 9/1998 | Yoon |
| 5,815,076 A | 9/1998 | Herring |
| 5,817,022 A | 10/1998 | Vesely |
| 5,817,092 A | 10/1998 | Behl |
| 5,820,553 A | 10/1998 | Hughes |
| 5,823,192 A | 10/1998 | Kalend |
| 5,828,770 A | 10/1998 | Leis |
| 5,830,144 A | 11/1998 | Vesely |
| 5,840,148 A | 11/1998 | Campbell |
| 5,868,673 A | 2/1999 | Vesely |
| 5,868,675 A | 2/1999 | Henrion |
| 5,879,297 A | 3/1999 | Haynor |
| 5,879,357 A | 3/1999 | Heaton |
| 5,895,235 A | 4/1999 | Droz |
| 5,902,238 A | 5/1999 | Golden |
| 5,902,310 A | 5/1999 | Foerster |
| 5,907,395 A | 5/1999 | Schulz |
| 5,910,144 A | 6/1999 | Hayashi |
| 5,913,820 A | 6/1999 | Bladen |
| 5,923,417 A | 7/1999 | Leis |
| 5,951,481 A | 9/1999 | Evans |
| 5,963,132 A | 10/1999 | Yoakum |
| 5,987,349 A | 11/1999 | Schulz |
| 5,989,265 A | 11/1999 | Bouquet De La Joliniere et al. |
| 6,015,390 A | 1/2000 | Krag |
| 6,019,725 A | 2/2000 | Vesely |
| 6,026,818 A | 2/2000 | Blair |
| 6,049,587 A | 4/2000 | Leksell |
| 6,052,477 A | 4/2000 | Wang |
| 6,059,734 A | 5/2000 | Yoon |
| 6,061,644 A | 5/2000 | Leis |
| 6,064,904 A | 5/2000 | Yanof |
| 6,067,465 A | 5/2000 | Foo |
| 6,076,008 A | 6/2000 | Bucholz |
| 6,082,366 A | 7/2000 | Andra et al. |
| 6,094,007 A | 7/2000 | Faul |
| 6,097,007 A | 8/2000 | Wang |
| 6,097,994 A | 8/2000 | Navab |
| 6,129,658 A | 10/2000 | Delfino |
| 6,129,668 A | 10/2000 | Haynor et al. |
| 6,130,612 A | 10/2000 | Castellano |
| 6,140,740 A | 10/2000 | Porat |
| 6,144,875 A | 11/2000 | Schweikard |
| 6,173,715 B1 | 1/2001 | Sinanan |
| 6,184,777 B1 * | 2/2001 | Mejia ........................ 340/10.1 |
| 6,198,963 B1 | 3/2001 | Haim et al. |

| | | | | | |
|---|---|---|---|---|---|
| 6,229,444 | B1 | 5/2001 | Endo et al. | FR | 26335259 | 2/1990 |
| 6,230,038 | B1 | 5/2001 | von Gutfeld et al. | JP | 8166446 | 6/1996 |
| 6,239,724 | B1 | 5/2001 | Doron | WO | WO-88/08282 | 11/1988 |
| 6,246,900 | B1 | 6/2001 | Cosman et al. | WO | WO-95/25475 | 9/1995 |
| 6,363,940 | B1 | 4/2002 | Krag | WO | WO-96/08208 | 3/1996 |
| 6,363,982 | B1 | 4/2002 | Nixon, Jr. | WO | WO-96/08999 | 3/1996 |
| 6,371,379 | B1 | 4/2002 | Dames | WO | WO-97/36192 | 10/1997 |
| 6,385,482 | B1 | 5/2002 | Boksberger | WO | WO-97/48438 | 12/1997 |
| 6,400,338 | B1 | 6/2002 | Mejia | WO | WO-98/30166 | 7/1998 |
| 6,401,722 | B1 | 6/2002 | Krag | WO | WO-98/40026 | 9/1998 |
| 6,405,072 | B1 | 6/2002 | Cosman | WO | WO-99/13775 | 3/1999 |
| 6,416,520 | B1 | 7/2002 | Kynast et al. | WO | WO-99/17133 | 4/1999 |
| 6,441,741 | B1 | 8/2002 | Yoakum | WO | WO-99/27839 | 6/1999 |
| 6,474,341 | B1 | 11/2002 | Hunter | WO | WO-99/30182 | 6/1999 |
| 6,492,885 | B1 | 12/2002 | Murata et al. | WO | WO-99/31082 | 6/1999 |
| 6,518,884 | B1 | 2/2003 | Tanji | WO | WO-99/35966 | 7/1999 |
| 6,618,939 | B2 * | 9/2003 | Uchibori et al. ............... 29/846 | WO | WO-99/44506 | 9/1999 |
| 6,675,810 | B2 | 1/2004 | Krag | WO | WO-99/58044 | 11/1999 |
| 6,698,433 | B2 | 3/2004 | Krag | WO | WO-99/58065 | 11/1999 |
| 6,701,179 | B1 | 3/2004 | Martinelli et al. | WO | WO-00/12009 | 3/2000 |
| 6,734,795 | B2 | 5/2004 | Price | WO | WO-00/24332 | 5/2000 |
| 6,812,842 | B2 | 11/2004 | Dimmer | WO | WO-00/51514 | 9/2000 |
| 6,822,570 | B2 | 11/2004 | Dimmer et al. | WO | WO-00/65989 | 11/2000 |
| 6,905,245 | B2 | 6/2005 | Cresens et al. | WO | WO-00/71047 | 11/2000 |
| 6,918,919 | B2 | 7/2005 | Krag | WO | WO-01/34049 | 5/2001 |
| 2002/0193685 | A1 | 12/2002 | Mate | WO | WO-01/54765 | 8/2001 |
| 2003/0088178 | A1 | 5/2003 | Owens et al. | WO | WO-02/199008 | 3/2002 |
| 2003/0117269 | A1 | 6/2003 | Dimmer | WO | WO-02/100485 | 12/2002 |
| 2003/0117270 | A1 | 6/2003 | Dimmer | | | |
| 2003/0192557 | A1 | 10/2003 | Krag | | | |
| 2004/0052034 | A1 | 3/2004 | Senba et al. | | | |
| 2004/0074974 | A1 | 4/2004 | Senba | | | |
| 2004/0127787 | A1 | 7/2004 | Dimmer | | | |
| 2004/0138554 | A1 | 7/2004 | Dimmer et al. | | | |
| 2004/0138555 | A1 | 7/2004 | Krag et al. | | | |
| 2005/0059884 | A1 | 3/2005 | Krag | | | |
| 2005/0154293 | A1 | 7/2005 | Gisselberg et al. | | | |

FOREIGN PATENT DOCUMENTS

| | | |
|---|---|---|
| EP | 0719420 | 7/1996 |
| EP | 1034738 | 9/2000 |

OTHER PUBLICATIONS

Hsiao, K., "Fast Multi-Axis Tracking of Magnetically-Resonant Passive Tags: Methods and Applications," Feb. 2001, Massachusetts Institute of Technology, Dept. of Electrical Engineering and Computer Science.

Kelley, William E., MD, Image-Guided Breast Biopsy: The ABBI* System, 1997, www.ussurg.com/health-care/procedures/abbi.

The World's Most Versatile Biopsy System Offered Only by USSC, ABBI* System Features, © 1997, United States Surgical Corporation, www.ussurg.com/health-care/procedures/abbi.

* cited by examiner

US 7,535,363 B2

MINIATURE RESONATING MARKER ASSEMBLY

CROSS-REFERENCE TO RELATED APPLICATIONS

This application is a divisional of U.S. application Ser. No. 09/954,700, filed Sep. 14, 2001, which issued on Nov. 14, 2006 as U.S. Pat. No. 7,135,978.

TECHNICAL FIELD

This invention relates to locating devices, and more particularly to miniature resonating marker assemblies and methods of tuning the same.

BACKGROUND OF THE INVENTION

Medical procedures often require locating and treating areas within a patient's body. Imaging systems, including x-ray, MRI, CT, and ultrasound have been used to help locate areas or particular targets within the body. While the imaging systems can be very useful in some situations, they can be limited to two dimensional information and may be unusable or difficult to use in certain procedures to provide real time three dimensional location information about a target.

Many noninvasive medical procedures, such as radiation therapy and surgical procedures, require precise location information about the target to minimize the extent of collateral damage to healthy tissue around the target. Markers have been used to locate targets on and in a patient's body in preparation for a medical procedure. One example includes the use of gold fiducials, which are solid, inert, metal beads that can be implanted in a patient at or near a tumor or other target that may be difficult to accurately detect using conventional imaging systems. The fiducial markers are passive markers that are easy to detect with imaging systems such as x-ray or ultrasound systems, but the passive markers do not provide active real-time location information during a medical procedure.

Active, implantable marker assemblies that generate a detectable signal have been used to locate a selected target or the like in real time. Many of the active markers are implantable in a patient, but they are hard-wired to a power source or other equipment external from the patient. These hard-wired markers are removed from the patient's body after a procedure or a series of procedures are concluded. The hard-wired markers are often fairly large in order to provide desired signal strength, clarity, or other performance characteristics needed during the procedure. The patient's body can typically temporarily handle the larger marker during the medical procedure before the marker must be removed. The removal process, however, requires an additional invasive procedure to the patient's body.

Leadless active markers also referred to as "wireless" active markers, have been developed to be implanted in a patient's body at or near a selected target, such as a tumor. The wireless active markers are typically activated or energized to generate a detectable signal used to locate the marker in the patient's body. Some wireless markers contain a power source, such as a battery, that provides the power to generate a signal detectable from outside the patient's body. The battery-powered markers, however, typically must be removed after the medical procedure because the caustic materials in the battery are not suitable to leave in a patient.

The conventional, wireless active markers are also often fairly large in order to provide a range of operating characteristics that allow the marker to be accurately located within the patient's body. Wireless active markers have experienced a trade-off between physical size and signal strength. Larger active markers have been needed to provide the required signal strength for detection and must be tuned adequately enough so that the detection system can detect the marker's signal. The large active markers, however, have drawbacks, including a reduced accuracy of determining the marker's precise location relative to a target, the degree of invasiveness needed to implant the markers in the body, and the costs of producing accurately tuned markers.

SUMMARY OF THE INVENTION

Under one aspect of the invention, a miniature resonating marker assembly is provided that overcomes drawbacks experienced in the prior art. In one embodiment, the resonating marker assembly includes a core, a wire coil composed of insulated wire disposed around the core, and a capacitor connected to the wire coil adjacent to the core. The core, coil, and capacitor form a signal element that, when energized, generates a magnetic field at the predetermined resonant frequency. The magnetic field has a magnetic center point positioned along at least one axis of the signal element. An inert encapsulation member encapsulates the signal element therein and defines a geometric shape of the resonating marker assembly. The geometric shape has a geometric center point substantially coincident with the magnetic center point along at least a first axis of the signal element. Accordingly, when a user locates the marker assembly's magnetic center point, the user will have also located the marker assembly's geometric center point. Conversely, when a user locates the marker assembly's geometric center, the user will have also located the marker assembly's magnetic center point.

In another embodiment, the miniature resonating marker assembly has a ferromagnetic core with an elongated central portion and two enlarged end portions attached to or integrally connected to the central portion. A first end portion has an axial thickness different from the thickness of the second end portion to define a core asymmetric about at least one axis through the marker assembly. A wire coil is disposed around the central portion of the core between the first and second enlarged end portions. A capacitor is connected to the coil adjacent to the core to form a signal element tuned to a selected resonant frequency. The magnetic center point of the signal element is substantially coincident with the geometric center point of the resonating marker assembly.

In another embodiment, the miniature resonating marker assembly has a core made of a material having a relative permeability greater than 1. The core has an elongated central portion and two endcaps connected to the central portion. One or more of the endcaps is axially movable relative to the central portion. A wire coil is disposed around the central portion of the core between the first and second endcaps. A capacitor, positioned adjacent to the core, is connected to the wire coil. Test equipment is attached and the resonant frequency is measured. The first endcap is movable relative to the coil and the core's central portion and is used to tune the circuit. Once the movable endcap is positioned at the desired location, the endcap is secured in place, the test equipment is removed from the circuit, and the signal element is completed by attaching the inductor lead to the capacitor terminal.

In another embodiment, the miniature resonating marker assembly has an elongated plastic sleeve with a wire coil disposed on the sleeve. A central portion of a core is placed within the sleeve, and a pair of endcaps are connected to the sleeve so that the coil is positioned between the endcaps. A capacitor is operatively connected to the wire coil and positioned adjacent to the core to form a signal element. The central portion of the core is axially movable relative to the sleeve and the coil and is used for tuning the marker assembly to a selected resonant frequency prior to completing the marker assembly.

In another embodiment, the miniature resonating marker assembly has a core with an end portion having a recess formed therein. A capacitor is positioned in the recess, and a wire coil is disposed around the core adjacent to the end portion and is operatively connected to the capacitor to form a signal element tuned to resonate at a selected frequency.

In another embodiment, the miniature resonating marker assembly has a core with a central portion and a pair of enlarged endcaps connected to the central portion. The central portion is made of a first material with a first magnetic permeability, and the endcaps are made of at least a second material with a second magnetic permeability different than the first magnetic permeability. A wire coil is disposed around the core between the endcaps, and a capacitor is operatively connected to the coil to form a tuned signal element.

In another embodiment, the resonating marker assembly has an annular-shaped capacitor with a central aperture, and an elongated ferromagnetic core extends through the aperture in the capacitor. A wire coil is disposed about the core and is connected to the capacitor. The wire coil has first and second portions. The first portion is disposed around the core on one side of the capacitor, and the second portion is disposed around the core on the other side of the capacitor.

In another embodiment, a method is provided for actively tuning the resonating signal element of a miniature marker during the manufacturing process. The method includes wrapping a first number of windings of an elongated wire around a central portion of a ferromagnetic core between a pair of endcaps to form a wire coil with the first number of windings. The coil with the first number of windings and the core form an inductor with a first inductance value. The first inductance value is actively measured and compared with a target inductance value. The number of windings forming the coil is then adjusted by adding or removing one or more windings from the core to form a coil With a second number of windings to form an inductor with a second inductance value substantially equal to the target inductance value.

In another embodiment, a method is provided for tuning a miniature resonating marker assembly to have a target resonant frequency by placing a core within a wire coil that has a plurality of windings. The core is made of a material with a relative permeability greater than 1. Lead lines of the wire coil are connected to a capacitor adjacent to the core to form a resonating marker unit. Test equipment is attached for measuring the resonant frequency. A first resonant frequency value of the resonating marker unit is measured and compared to the target resonant frequency value. The core is moved axially relative to the wire coil to adjust the resonant frequency value of the resonating marker unit to a second resonant frequency value substantially equal to the target resonant frequency value. The core is secured in a fixed location relative to the coil and the capacitor after the target resonant frequency value is reached. After retesting to confirm that the desired resonant frequency has been achieved, the test equipment is removed. (Lead lines have already been connected as stated above.) Once the circuit has been completed, neither the inductance nor the capacitance of the individual components can be directly measured. However, the impedance and phase angle of the tuned circuit can be measured which allows the resonant frequency and the quality factor (Q factor) of the tuned circuit to be determined.

DETAILED DESCRIPTION OF THE INVENTION

In the following description, certain specific details are set forth in order to provide a thorough understanding of various embodiments of the invention. However, one skilled in the art will understand that the invention may be practiced without these details. In other instances, well-known structures associated with resonating markers and activators have not been shown or described in detail to avoid unnecessarily obscuring the description of the embodiments of the invention.

Figure 1:
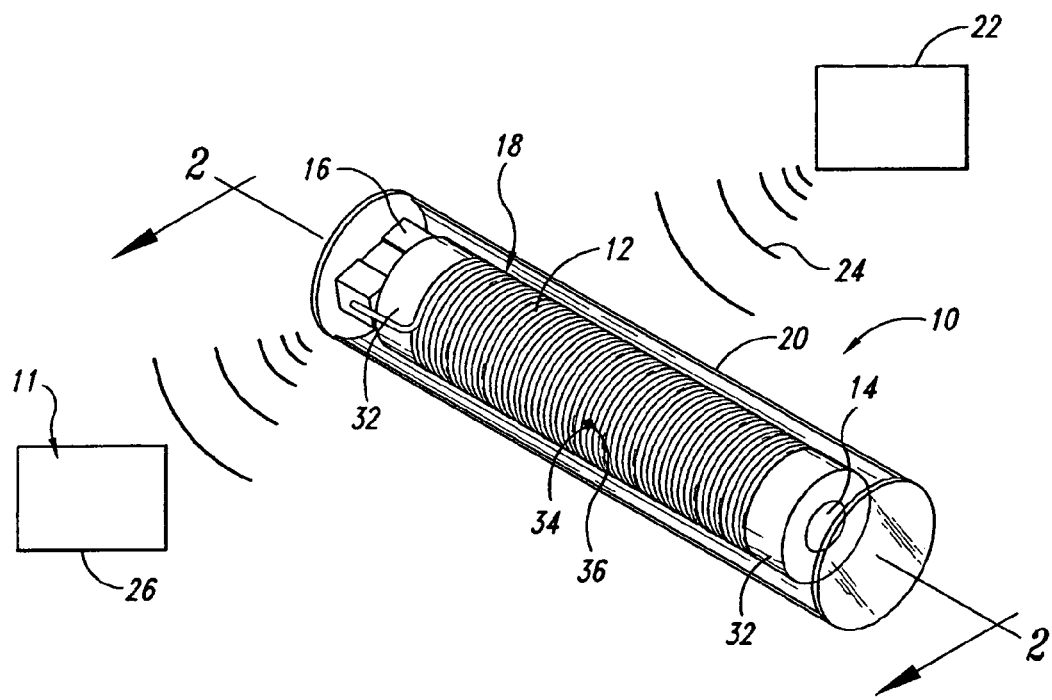
FIG. 1 is an isometric view of an implantable miniature resonating marker assembly in accordance with one embodiment of the present invention.

FIG. 1 is an isometric view of an implantable miniature resonating marker assembly 10 in accordance with one embodiment of the present invention. The marker assembly 10 is an inert, activatable assembly that can be excited to generate a signal at a resonant frequency detectable by a marker detection system external to the patient. An example of the marker detection system is described in detail in copending U.S. patent application Ser. No. 09/877,498, entitled Guided Radiation Therapy System, which is incorporated herein in its entirety by reference thereto.

The marker assembly 10 includes a coil 12 wound around a ferromagnetic core 14 to form an inductor. The inductor is connected to a capacitor 16, so as to form a signal element 18. Accordingly, the signal element 18 is an inductor (L) capacitor (C) series circuit. The signal element 18 is enclosed and sealed in an encapsulation member 20 made of plastic, glass, or other inert material. Accordingly, the marker assembly 10 is a fully contained and inert unit that can be used, as an example, in medical procedures in which the marker assembly is secured on and/or implanted in a patient's body.

The marker assembly 10 can be activated by an external excitation source(s) 22, so the signal element 18 generates a detectable signal that allows the marker assembly to be precisely located, for example, during a medical procedure. The excitation source 22, in one embodiment, generates a magnetic field 24 at a selected frequency that substantially matches the resonant frequency of the specifically tuned marker assembly 10. When the marker assembly 10 is excited by the magnetic field 24, the signal element 18 generates a response signal at the resonant frequency 90 degrees out of phase with the magnetic field. The marker assembly 10 is constructed, as discussed in detail below, to provide an appropriately "loud" and distinct signal by optimizing marker characteristics, such as the quality factor, for example, and by providing an accurate and precise means of tuning the marker to a predetermined frequency to allow reliable detection by the marker detection system 11. The signal from the accurately tuned marker assembly 10 is sufficient to allow the marker detection system 11 to determine the marker assembly's identity, precise location, and orientation in three dimensional space.

The miniature marker assemblies 10 discussed below are accurately tuned to a chosen resonant frequency. Because the miniature marker assemblies 10 are constructed to be very small, the markers must be tuned so that, when energized, they will provide a response signal that is strong and clearly distinguishable from the excitation signal, signals from other markers, and environmental noise. Accordingly, the signal will have a strength, clarity, and uniqueness that can be detected and analyzed by the sensor system 26 to determine the precise location of the marker assemblies 10 on and/or within the patient relative to the sensor system. The information regarding the precise location and orientation of the marker assemblies 10 and the target areas is then usable to help minimize collateral damage to healthy tissues around the targets during radiation therapy, surgical procedures, or other selected medical procedures that require locating and tracking a specific tissue or area for monitoring or treatment purposes.

Figure 2:
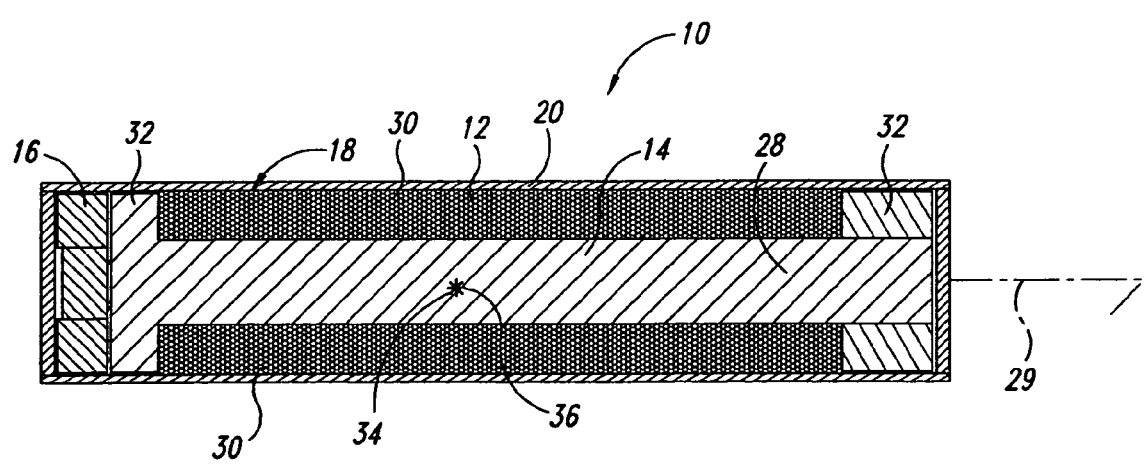
FIG. 2 is a cross-sectional view of the marker assembly taken substantially along line 2-2 of FIG. 1.

FIG. 2 is a cross-sectional view of the miniature resonating marker assembly 10 of FIG. 1. The marker assembly 10 of one embodiment has a generally cylindrical shape with an axial dimension of approximately 2-14 mm, and a diameter of approximately 0.5-3.0 mm, inclusive. In other embodiments, the marker assembly 10 can have other dimensions and the above range of dimensions is provided as an illustrative example of the size of one embodiment of the marker assembly. The marker assembly 10 has the wire coil 12 formed from an elongated insulated copper wire tightly wound around the core 14.

In the illustrated embodiment, the core 14 is a material having a relative permeability greater than 1, such as a ferromagnetic material. In one embodiment, the core 14 is made from a selected ferromagnetic material, such as Fair Rite 78. The core 14 includes an elongated central portion 28 and a pair of enlarged ferromagnetic endcaps 32 attached to the ends of the central portion 28. The endcaps 32 in the illustrated embodiment are ferromagnetic endcaps. The wire coil 12 is wound around the central portion 28 between the endcaps 32. In the illustrated embodiment, the endcaps 32 are substantially cylindrical and each has an outer diameter approximately the same as the outer diameter of the coil 12.

Figure 3:
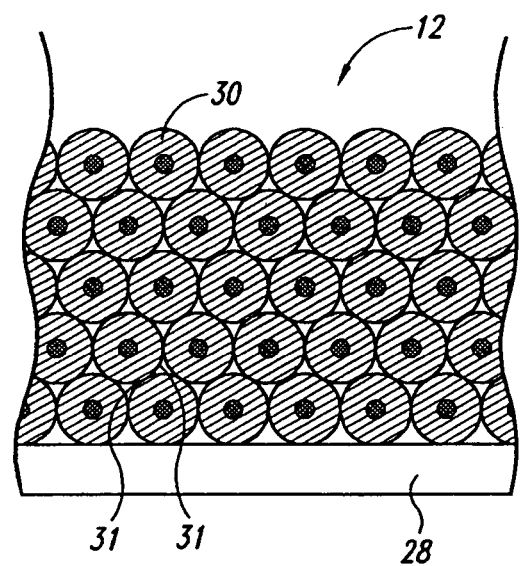
FIG. 3 is an enlarged cross-sectional view of a plurality of windings on the marker assembly of FIG. 1.

The wire coil 12 in the illustrated embodiment is made up of approximately 100-3,000 windings 30 of a low resistance, small diameter, insulated wire (e.g., 45-54 AWG, American Wire Gauge) tightly wound around the core's central portion 28. The number of windings 30 in the coil 12 depends upon the wire type, the wire size, the wire shape, the number of wires, the wind geometry, the core size, the core's material, the core's geometry, and the inductance required to tune the signal element 18. As shown in FIG. 3, the coil 12 is formed by a large number of windings 30 wound onto the core's central portion 28 so that each winding is immediately adjacent to all of its nearest neighbors. For wire with a round cross-section as shown in FIG. 3, each winding, thus, will be immediately adjacent to up to six nearest neighbors. Accordingly, each winding 30 is nested in the valley area 31 formed between adjacent windings to provide a tightly packed winding configuration with the maximum number of windings within the volume between the endcaps. The tightly packed coil 12 on the ferromagnetic core's central portion 28 allows for a high inductance value to be achieved for the miniature marker assembly's small volume.

Alternatively, especially at higher frequencies, it may be desirable to increase the distance between the coiled wires in a way that does not result in random winding. One way to increase the distance in a predictable and repeatable manner is to use insulated wire having a thicker insulation coating around the wire filament. Accordingly, the wire filaments in adjacent winds are spaced further apart, even though the insulated wire is wound in the tightly packed configuration shown in FIG. 3. Another embodiment can use two (or more) parallel strands of wire wound to form the coil, wherein only one of the wires, an active wire, is connected to the capacitor. The other wire is a spacer wire that forms a spacer wind between each wind of the active wire. Therefore, the separation distance between consecutive winds of the active wire is increased.

Another way to increase the distance between adjacent winds in an organized but less tightly packed configuration is to place each wind on top of adjacent windings rather than in the valley area 31. In this configuration the coil is wound such that each wire is adjacent to only four of its nearest neighbors.

As best seen in FIGS. 1 and 2, the elongated cylindrical marker assembly 10 of the illustrated embodiment has a geometric center point 34. The geometric center point 34 can be determined by locating the midpoint along each of the marker assembly's length, width, and depth. A user can determine the geometric center point 34 of an implanted marker assembly 10 if needed by conventional techniques such as taking an image of the assembly with an x-ray or ultrasound device and physically measuring the image of the assembly. The spatial relationship of the geometric center point 34 relative to the target or other marker assemblies 10 may also be visually identified. When the marker is viewed using commonly used modalities such as x-ray, it is functioning similar to a surgical clip or other devices used to mark a specific tissue or region.

The signal element 18 in the marker assembly 10 also generates a magnetic field when the signal element is excited, and the magnetic field has a magnetic center point 36. If the core 14 was a symmetrical member about the X, Y, and Z axis, the endcaps 32 would be the same size, and the magnetic center point 36 would be offset from the marker assembly's geometric center point 34. The core 14 of the illustrated embodiment, however, is an asymmetric core with endcaps 32 having different thicknesses. The core 14 is shaped and sized so that the magnetic center 36 of the signal element 18 is coincident with the geometric center 34 of the marker assembly 10.

The asymmetric configuration of the core 14 effectively shifts the center of the magnetic field axially along the length of the core. The signal element 18 can be configured and positioned in the encapsulation member 20 so that the geometric and magnetic centers 34 and 36 are coincident with each other. The coincident orientation of the geometric and magnetic centers 34 and 36 allows a physician or technician to nonvisually determine the precise location of an implanted marker assembly 10 relative to a target during a medical procedure.

As an example, the marker assembly 10 can be implanted either permanently or short-term in a patient and located visually with an imaging system to determine the marker assembly's position and location relative to the target before initiating a selected medical procedure. The physician or technician can visually determine the marker assembly's geometric center 34 relative to the target. The information about the geometric center 34 relative to the target can be utilized to provide patient set-up procedures or a treatment plan. The physician or technician will know that, when the marker assembly 10 is excited via the excitation source(s) 22 (FIG. 1) and the location of the magnetic center 36 is nonvisually determined in three-dimensional space, the magnetic center is at the same location as the geometric center 34 and has the same relative orientation to the target. Accordingly, the marker assembly 10 can provide extremely accurate nonvisual information regarding the marker assembly's actual real time location within the patient's body relative to the target. That location information can be used to minimize the margins needed around the target when performing a medical procedure. If the geometric center point 34 and the magnetic center point 36 are displaced by even small amounts, the margins around the target may need to be larger, thereby potentially having a greater impact on healthy tissue around the target.

The asymmetric core 14 illustrated in FIG. 2 is shown as having a generally cylindrical shape with the rod-shaped central portion 28 and disk-shaped endcaps 32. In alternate embodiments, the endcaps 32 can have other shapes, such as arcuate or semispherical shapes, that help to achieve the required characteristics of the tuned marker assembly 10.

For marker assemblies that will be implanted, it is highly desirable to minimize the size of the marker assembly 10 to allow for accurate and minimally invasive placement of the assembly into body tissues and cavities via such methods as introducer needles, endoscopes, catheters, etc. There are trade-offs, however, between marker size and signal strength, because smaller markers typically provide weaker signals. Therefore, the miniature marker assembly 10 should be as small as possible while still providing an adequate response signal over environmental noise when energized by the excitation source(s) 22. To maximize the signal strength of the marker assembly 10, the outer diameter of the coil 12 and ferromagnetic core 14 should be maximized relative to the outer dimension of the marker assembly. The marker assembly 10 of the illustrated embodiment accomplishes this, in part, because the capacitor 16 and any other components, such as a tissue fastener 29 (illustrated in phantom lines connected to the marker assembly), are axially aligned with the core 14 and positioned at the proximal or distal ends of the core. The size constraints for markers placed on the body are less stringent than for implanted markers.

Figure 4:
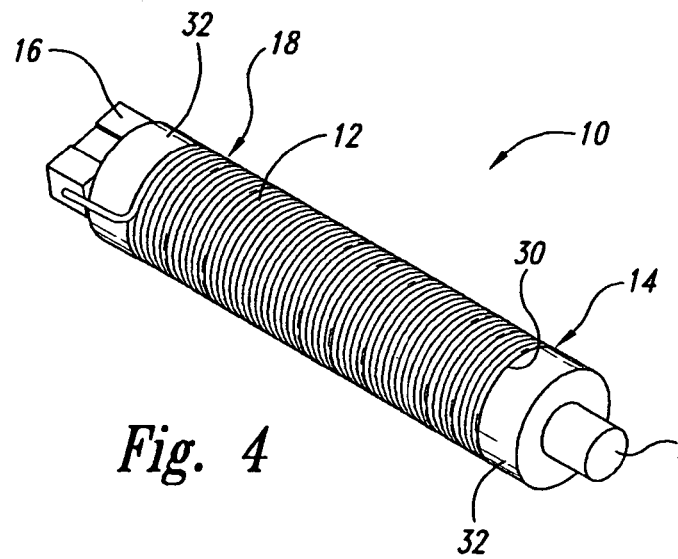
FIG. 4 is an isometric view of a tunable resonating marker assembly in accordance with an alternate embodiment of the present invention, an endcap of the assembly shown in a first adjusted position for tuning the marker assembly.
Figure 5:
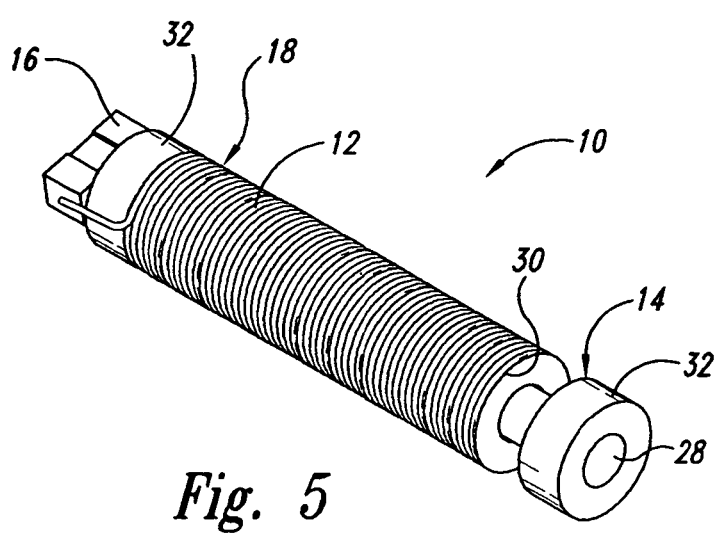
FIG. 5 is an isometric view of the resonating marker assembly of FIG. 4 with an endcap in a second adjusted position for tuning the marker assembly.

FIG. 4 is an isometric view of the tunable miniature marker assembly 10 with an adjustable endcap 32 shown in a first position. FIG. 5 is an isometric view of the marker assembly 10 of FIG. 4 with the endcap 32 in an axially adjusted second position for tuning of the marker assembly. In one scenario, the miniature marker assembly 10 is accurately tuned to provide the maximum signal strength at the resonant frequency with a maximum quality factor for the signal. A primary factor in tuning the marker assembly 10 is determining when the impedance phase shift at the frequency of interest is equal to zero. The impedance phase shift becomes zero when the capacitor impedance and the inductor impedance are matched for a given frequency. Alternatively, the marker could be tested in a wireless fashion where the phase shift at the resonant frequency of the marker would be 90 degrees out of phase when measured at the sensor system 26 (FIG. 1). When the signal element 18 is accurately tuned so the capacitor and inductor impedances are matched for a given frequency, the signal element 18 will resonate at that selected frequency.

In the illustrated embodiment of FIGS. 4 and 5, one of the endcaps 32 has an aperture therein that receives the core's central portion 28. The endcap 32 is axially movable on the core's central portion 28 relative to the coil 12 when the signal element 18 is being tuned. When the adjustable endcap 32 is positioned immediately adjacent to and abutting the coil 12 (FIG. 4), the endcap is positioned to reduce the inductance of the inductor, thereby increasing the resonant frequency of the marker assembly 10. When the adjustable endcap 32 is positioned at the end of the core's central portion 28 spaced apart from the coil 12, the endcap is positioned to maximize the inductance of the inductor thereby decreasing the resonant frequency of the marker assembly. Accordingly, axial movement of the endcap 32 relative to the coil 12 can increase or decrease the resonant frequency to fine tune the signal element 18.

During the manufacturing process of the marker assembly 10, the endcap 32 is axially adjusted to precisely tune the marker assembly. In one embodiment, the entire signal element 18 is assembled with the exception of the movable endcap 32. The movable endcap 32 is then slipped onto the end of the core's central portion 28 and positioned axially toward the coil 12 to achieve the required inductance to obtain the desired resonant frequency.

The axial position of the ferromagnetic endcap 32 can be determined by axially moving the endcap 32 and simultaneously measuring the impedance phase shift at the frequency of interest with an impedance analyzer. The impedance analyzer is connected to the coil's lead wires that connect to the capacitor 16. When the impedance analyzer determines that the phase shift is equal to zero, the capacitor impedance and the inductor impedance are matched for the selected frequency. The endcap 32 is then secured in place on the core's central portion 28 with an adhesive, such as a UV-cured or heat-cured epoxy.

The above process of tuning the miniature marker assembly 10 allows for extremely accurate tuning during mass production of the marker assemblies while minimizing the degree of variation between two marker assemblies tuned to the same frequency. The signal elements 18 of marker assemblies 10 having a tuning accuracy in the range of ±0.5% of the desired resonant frequency can be economically manufactured in large quantities. In one embodiment, signal elements 18 can be economically tuned consistently during manufacturing with a margin of error as low as ±0.2% of the desired resonant frequency.

In another embodiment, the resonant frequency of the signal element 18 can be finely tuned by removing material from the ferromagnetic core 14 by, as an example, laser cutting or machining ferromagnetic material from an endcap 32 or the core's central portion 28. In another embodiment, fine tuning of the signal element 18 can be accomplished by removing material from the capacitor 16. The resonant frequency of the signal element 18 can be actively or dynamically measured during the material removal process to determine when the phase shift is zero and inductive reactance equals the capacitive reactance of the signal element.

After the endcap 32 is fixed in position on the core's central portion 28, the tuned signal element 18 can be carefully slid into the encapsulation member 20 (FIG. 1). The encapsulation member 20 is sealed to provide a fully contained inert miniature marker assembly 10 specifically tuned to a selected frequency. One of the fragile areas of the marker assembly 10 can be the connection between the capacitor 16 and the wire leads from the coil 12. The connections can be susceptible to damage during the manufacturing process because of the small diameter of the coil wire. Therefore, the signal element 18 must be carefully inserted into the encapsulation member 20. In one embodiment, the capacitor/coil interface is sealed with a flexible epoxy or other adhesive that electrically insulates the lead wires. Sealing the lead wires also protects the lead wires from corrosion if any fluid from the patient tissue contacts the signal element 18.

Figure 6:
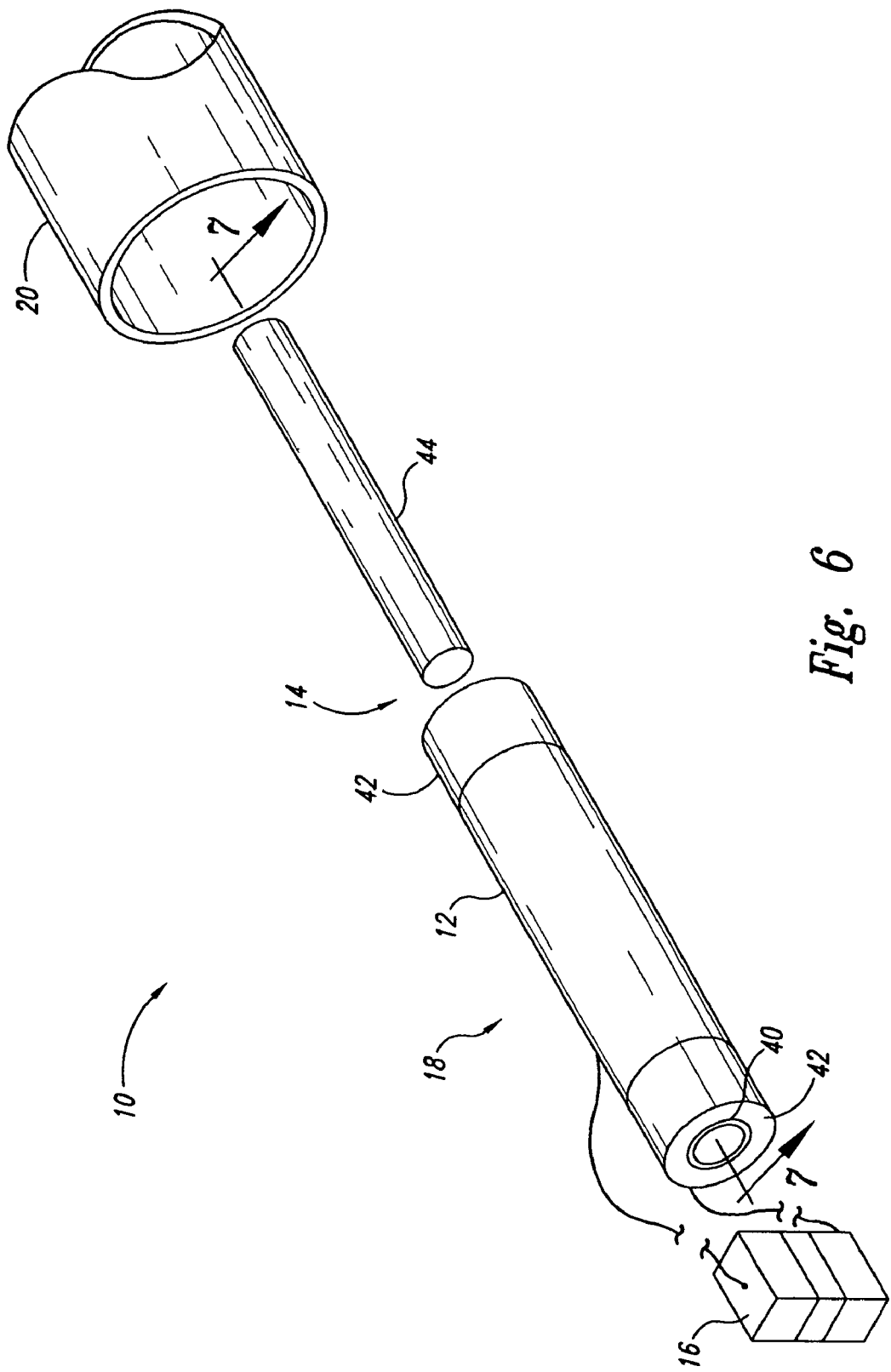
FIG. 6 is an exploded isometric view of a miniature resonating marker assembly in accordance with an alternate embodiment of the present invention.
Figure 7:
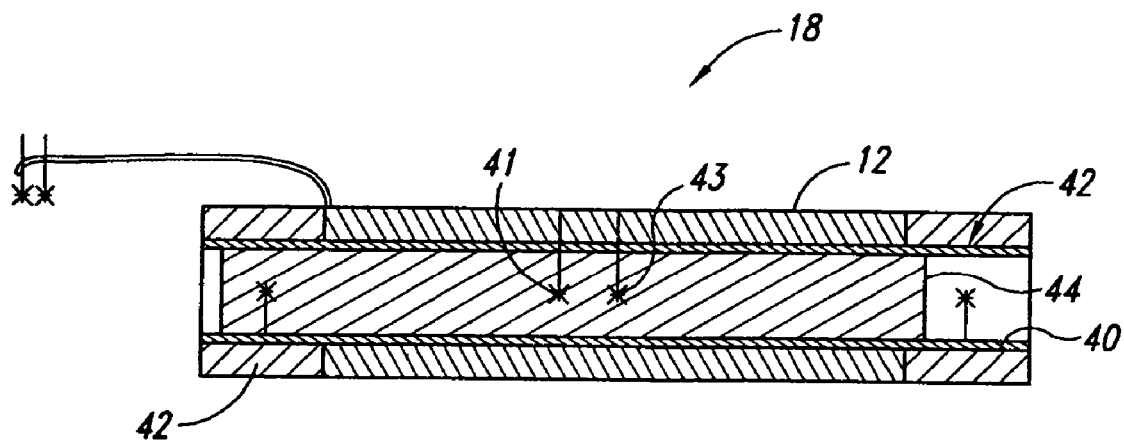
FIG. 7 is a cross-sectional view taken substantially along line 7-7 of FIG. 6 showing a miniature inductor of the marker assembly with a ferromagnetic core in an off-set position.

FIG. 6 is an exploded isometric view of a marker assembly 10 of an alternate embodiment. FIG. 7 is a cross-sectional view taken substantially along line 7-7 of FIG. 6 showing the inductor portion of the marker assembly 10 in an assembled condition. The marker assembly 10 includes a plastic sleeve 40 on which the coil 12 is wound. In this illustrated embodiment, the ferromagnetic core 14 is made of two ferromagnetic endcaps 42 and a separate ferromagnetic rod 44. The ferromagnetic endcaps 42 are positioned on the ends of the plastic sleeve 40, and the coil 12 is positioned between the endcaps. The ferromagnetic rod 44 is shaped and sized to slide into the plastic sleeve 40. During the manufacturing and tuning of the marker assembly 10, the ferromagnetic rod 44 is axially movable in the sleeve relative to the coil 12 and the ferromagnetic endcaps 42 to change the resonant frequency.

In the illustrated embodiment, a preformed plastic sleeve 40 is used in the coil winding process so the coil 12 is wound directly onto the sleeve in the tight winding configuration as discussed above. The ferromagnetic endcaps 42 can be adhered to the plastic sleeve 40 either before or after the winding process. After the coil 12 and the ferromagnetic endcaps 42 are securely positioned on the plastic sleeve 40, the ferromagnetic rod 44 is inserted into the plastic sleeve and axially positioned relative to the coil 12 until the target resonant frequency of the signal element 18 is achieved. In one embodiment, the resonant frequency is measured dynamically as the ferromagnetic rod 44 is adjusted axially relative to the coil 12 until the inductive reactance matches the capacitive reactance. This dynamic measuring of the resonant frequency allows the ferromagnetic rod 44 to be precisely positioned during tuning of the marker assembly 10. Accordingly, the marker assembly 10 provides the maximum tunability to a desired inductance for a given frequency.

As best seen in FIG. 7, the ferromagnetic rod 44 is positioned in the plastic sleeve 40 coaxially with respect to the coil 12 such that the geometric centers 41 and 43 of the rod and the coil, respectively, are offset by a selected distance when a target resonant frequency is nominally achieved. The ferromagnetic rod 44 can then be moved axially in either direction to increase or decrease the resonant frequency to accommodate the maximum variation possible in the coil 12 or the capacitor 16 while still obtaining the target resonant frequency. The axial adjustments of the ferromagnetic rod 44 can be minimal because the inductance changes exponentially as a function of the distance between the geometric center 43 of the coil 12 and the geometric center 41 of the ferromagnetic rod. Thus, axial movement of the ferromagnetic rod 44 provides extremely fine tuning of the marker assembly's signal element 18 with a minimum degree of axial movement.

Once the ferromagnetic rod 44 is positioned in the plastic sleeve 40 to achieve the specific inductance, thereby tuning the signal element 18 to resonate at a selected frequency, the ferromagnetic rod is securely affixed in position with an adhesive. In one embodiment, the adhesive is a UV-cured epoxy, a polyurethane adhesive, or a ferromagnetic-based adhesive. In the case of the ferromagnetic-based adhesive, the uncured adhesive should be present in the bond line joint during tuning so that the resonant frequency does not shift. The tuned signal element 18 is then encapsulated in the inert encapsulation member 20 (FIG. 1) as discussed above.

In a simpler alternate configuration, ferromagnetic endcaps are not incorporated in the signal element 18 and the ferromagnetic core 14 may be just the ferromagnetic rod 44 having a length the same as the coil 12, shorter than the coil, or longer than the coil. The signal element 18 is then tuned by moving the ferromagnetic rod 44 within the coil 12, which may or may not be wound on a plastic sleeve. Ferromagnetic paste or adhesive may also be used in place of preformed rigid ferromagnetic cores. In this configuration, the signal element is tuned to a specific resonant frequency by injecting ferromagnetic paste into the center of the coil.

The encapsulation member 20 can be a plastic or glass sleeve sealed on both ends so as to fully enclose the tuned signal element 18. For marker assemblies 10 designed for use in medical procedures in which the marker assemblies may be permanently implanted in a patient, the signal elements 18 are encapsulated in part to protect the patient's tissues from exposure to any non-biocompatible materials that may be used to optimize the marker signals. The encapsulation member 20 also insulates the signal element 18 from bodily fluids that may cause corrosion or oxidation of the signal element and affect its performance. The encapsulation member 20 hermetically seals the signal element 18 without adversely affecting the signal element or its emitted signal.

In one embodiment the signal element is encapsulated in a strong, rigid, and biocompatible material such as epoxy that helps protect the signal element 18 from mechanical damage.

Figure 8:
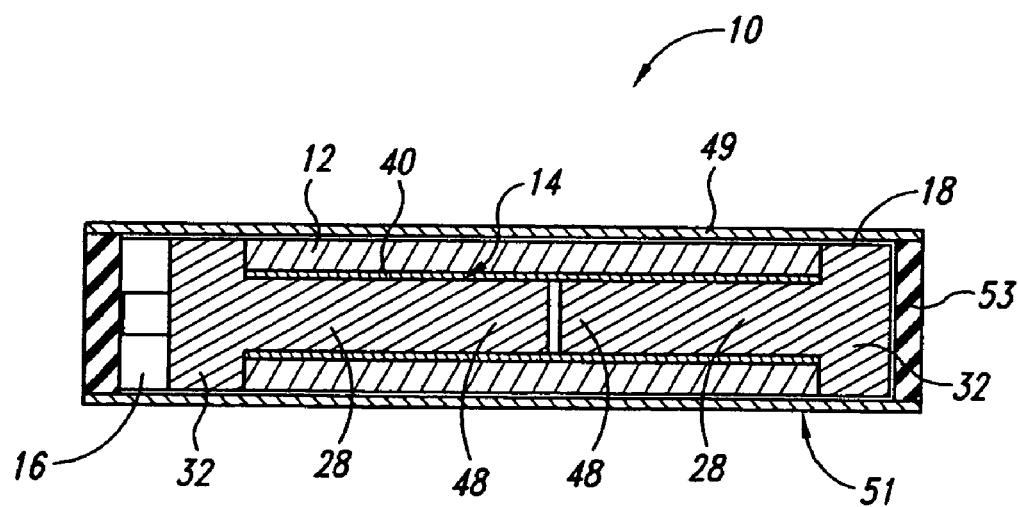
FIG. 8 is a cross-sectional view of a miniature resonating marker assembly in accordance with an alternate embodiment, with a two-piece ferromagnetic core.

Alternatively, the signal element 18 can be placed inside of a biocompatible encapsulation sleeve 49 as shown in FIG. 8. The encapsulation sleeve 49 and signal element 18 form an assembly 51 that can be completely encased in a biocompatible material, such as UV-cured or heat-cured epoxy 53. Alternatively, rather than potting the entire assembly 51, another encapsulating material, such as epoxy, could be injected inside the encapsulation sleeve 49 to encase the signal element 18 so that the outer wall of the plastic or glass encapsulation sleeve is in direct contact with the tissue. Materials that are appropriate for plastic encapsulation sleeves 49 can include, as an example, polyamide, polyetherblockamide, polyimide, polyurethane, polyetheretherketone. Biocompatible glass may also be an acceptable material for encapsulation sleeves 49.

Some benefits of using an encapsulation sleeve 49 are that the sleeve can be used to help center the signal element 18, help to prevent damage to the signal element during handling, and help make the encapsulation process easier by preventing the signal element from being exposed during encapsulation. For example, if the signal element 18 was not placed in an encapsulation sleeve 49 prior to potting with epoxy, the signal element may move to the side of the mold and be exposed after the epoxy had cured. To prevent this phenomena from occurring, the signal element 18 needs to be placed in a sleeve 49 or otherwise coated before completing the final encapsulation process.

In another embodiment, the encapsulation member 20 is composed of sturdy, durable, biocompatible heat-shrink tubing. The signal element 18 is placed in the heat-shrink material, and heat is applied until the material shrinks and encases the signal element. The heat-shrink material is selected so that the heat necessary to shrink the material is not high enough to damage the signal element 18. In an additional embodiment, the signal element 18 and the shrunken encapsulating sleeve are potted in epoxy to fully enclose and seal the signal element 18.

The signal element 18 in other embodiments can be encapsulated with one or more materials. Using multiple materials can make the encapsulation process easier and can allow additional functionality to be incorporated into the marker assembly 10. As an example, the signal element 18 can be encapsulated with a rigid biocompatible material, such as an epoxy, to protect the components from damage. The epoxy also would provide a rigid base for, as an example, attaching a fastener for mechanically attaching the marker assembly to tissue in the patient, thereby preventing the marker assembly from migrating immediately following marker deployment in the patient and during the implant duration.

An additional biocompatible coating material may be placed on the outside of the rigid encapsulation member 20 to react with the tissue and help the marker assembly 10 adhere to the tissue. The additional coating material can also help promote or accelerate tissue encapsulation of the marker. Eliciting a specific biological response at the marker/tissue interface could also be beneficial in preventing marker assembly migration, especially in soft tissue.

In another embodiment, the encapsulation member 20 includes a biocompatible, thin-walled glass or plastic vial. These vials are similar to the previously described encapsulation sleeves 49 except one end is already sealed prior to insertion of the signal element 18. The signal element 18 is placed into the vial and an encapsulation material, such as a quick-curing adhesive or epoxy, is injected into the vial to fully encase the signal element. After the signal element 18 is placed in the vial, the epoxy or other material is dispensed into the vial so as to avoid entrapping air bubbles in the vial. Avoiding air bubbles is important because if the vial is damaged at the site of a large bubble, part of the signal element may be exposed to body fluids and tissues. When the signal element 18 is placed in the previously discussed glass or plastic small-bore sleeve, epoxy can be injected into the sleeve to more easily avoid the formation of air bubbles within the sleeve.

Using glass can be advantageous because glass is inert and insoluble. The characteristics of glass are also very desirable for long-term implantation of marker assemblies. If undamaged, the glass will prevent leakage (egress) of incompatible materials from the signal element 18 and ingress of tissue fluids to the signal element. In another embodiment, powdered or granular glass is combined with biocompatible epoxy and used to encapsulate the signal elements 18 placed in sleeves or vials. In another embodiment the signal element 18 can be secured with an adhesive inside an encapsulation sleeve or vial and the end(s) of the sleeve/vial can be closed using heat or a laser to melt and seal the end(s) of the vial or sleeve.

FIG. 8 is a cross-sectional view of a marker assembly 10 of an alternate embodiment. The marker assembly 10 has the plastic sleeve 40 around which the coil 12 is wound. The ferromagnetic core 14 is a two-piece core, with each core piece 48 having an endcap 32 and a first section of the core's central portion 28 integrally connected to each other. Each core piece 48 is positioned so that the section of the core's central portion 28 extends into the plastic sleeve 40 until the endcap 32 is adjacent to the coil 12. The two core pieces 48 are coaxially aligned and immediately adjacent to each other within the plastic sleeve 40.

Tuning of the marker assembly's 10 signal element 18 is achieved by axially moving one or both of the core pieces 48 relative to each other and to the coil 12. The resonant frequency can be actively measured during the axial movement of one or both of the core pieces 48 until the inductive reactance of the signal element 18 and the capacitive reactance are matched for the selected frequency. After the marker assembly's signal element 18 has been accurately tuned to resonate at the selected frequency, the core pieces 48 are fixed in position relative to the plastic sleeve 40 and the coil 12 by an adhesive. The signal element 18 can be inserted into an encapsulation member and hermetically sealed to provide the fully enclosed and inert miniature marker assembly 10 suitable for implantation in a patient.

Figure 9:
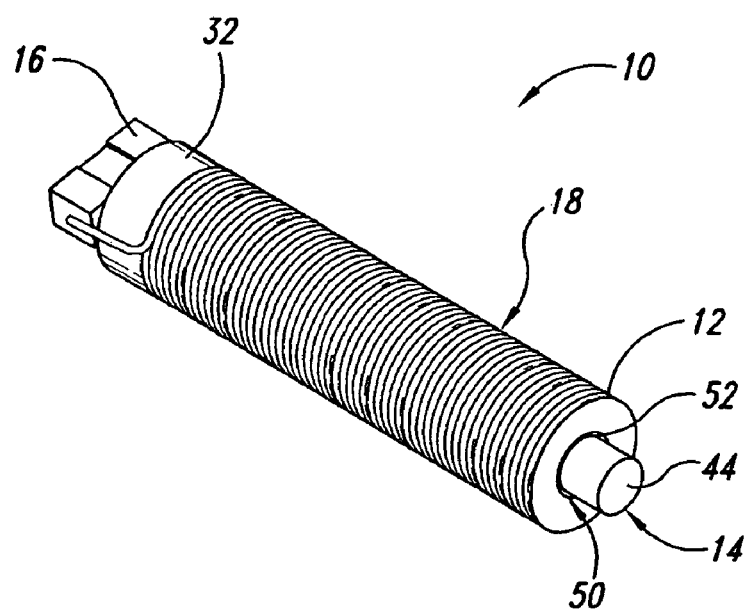
FIG. 9 is an isometric view of a miniature resonating marker assembly in accordance with an alternate embodiment utilizing a ferromagnetic paste between a ferromagnetic core and the wire coil. For the purposes of clarity, the second ferromagnetic endcap is omitted from this figure.

FIG. 9 is an isometric view of a marker assembly 10 in accordance with another alternate embodiment. In this embodiment, the marker assembly 10 includes the capacitor 16, the coil 12 connected to the capacitor, and the ferromagnetic core 14. The core 14 includes a ferromagnetic rod 44 extending through the coil 12, and endcaps 32 are attached to the ferromagnetic rod. In FIG. 9, an endcap 32 on the signal element opposite the capacitor 16 and the encapsulation member 20 are not shown for illustrative purposes. The coil 12 in this embodiment is made from an elongated wire having an outer airbondable coating that is on top of the wire insulation. Prior to winding the wire around, as an example, a manufacturing machine's mandrel, the airbondable wire is heated to make the coating sufficiently tacky so that the wire adheres to adjacent windings as it is wound to form the coil 12. After the coil 12 has been wound, the airbondable coating has set, and the coil has been removed from the manufacturing machine's mandrel, the coil is a freestanding coil with an open interior area 50.

In the illustrated embodiment, a coil winding machine is used to wind the coil 12 onto a metal mandrel and then eject the coil off the mandrel. Winding the coil 12 onto a metal mandrel has benefits over winding directly onto the small diameter (e.g., 0.75 mm) ferromagnetic rod 44 because the ferromagnetic rod must be supported on both ends to prevent fracture and/or breakage. Securely holding the ferromagnetic rod 44 with a spindle and tail stock of the winding machine requires concentricity of the small components, because slight misalignment can also lead to fracture and/or breakage of the ferromagnetic rod. Winding the coil 12 onto a metal mandrel of a coil winding device rather than directly onto the ferromagnetic core 44 is more conducive to a fully automated process because the small ferromagnetic core does not have to be preloaded prior to starting the winding process.

The core 14 is positioned so the ferromagnetic rod 44 extends through an interior area 50 in the coil 12. The coil's interior area 50 is sized to provide a clearance fit with the ferromagnetic rod 44, so there is a slight space between the ferromagnetic rod and the inner wall of the coil 12. A ferromagnetic-based adhesive 52 can be used at the interface between the ferromagnetic rod 44 and the coil 12 during assembly to eliminate the air gap between the components, to provide additional ferromagnetic material within the coil, and to secure the ferromagnetic rod 44 to the coil 12. Adding additional ferromagnetic increases the inductance of the signal element 18 without increasing the signal element's size. The endcaps 32 are attached to the ends of the ferromagnetic rod 44 with the coil 12 between them.

The signal element 18 can be tuned to the selected resonant frequency by axially adjusting the ferromagnetic rod 44 and/or an endcap 32 relative to the coil 12. Once the signal element 18 is precisely tuned, the adhesive 52 is allowed to set or cure, and the ferromagnetic rod 44 is fixed in position in the coil 12 and the endcap 32 is fixed in position on the ferromagnetic rod. The tuned signal element 18 can then be positioned in an encapsulating member 20 (FIG. 1) to provide the inert miniature resonating marker assembly 10.

Figure 10:
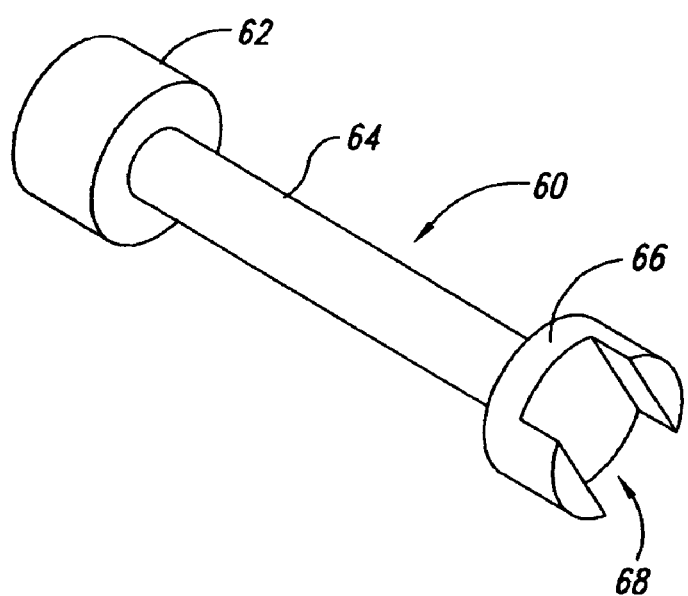
FIG. 10 is an isometric view of a ferromagnetic core of a miniature resonating marker assembly in accordance with an alternate embodiment, the core having a recess that receives a capacitor (not shown).
Figure 11:
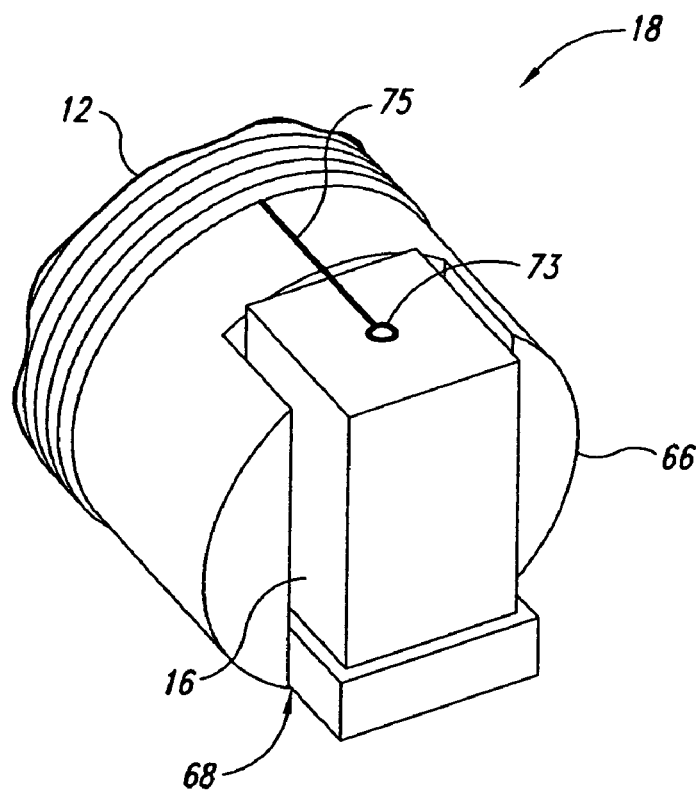
FIG. 11 is an enlarged isometric view of an endcap of the core of FIG. 10 with the capacitor shown positioned within the recess.

FIG. 10 is an isometric view of an alternate embodiment of a ferromagnetic core 60 of a marker assembly 10. FIG. 11 is an enlarged isometric view of a recessed endcap 66 of the core 60 of FIG. 10. The core 60 (FIG. 10) of the illustrated embodiment has an enlarged, substantially solid endcap 62 connected to one end of a smaller diameter ferromagnetic rod 64, and a second endcap 66 is attached to the opposite end of the ferromagnetic rod. The second endcap 66 has a recess 68 shaped and sized to receive a capacitor 16 (FIG. 11) therein. The capacitor 16 in the illustrated embodiment is securely retained in place within the recess 68 by a non-conductive adhesive. The coil 12 is wound around the ferromagnetic rod 64 and operatively connected to the terminals 73 of the capacitor 16 so as to form the signal element 18.

The recess 68 in the endcap 66 can be formed by grinding, molding, or laser cutting the endcap. The recess 68 is designed to position the capacitor 16 in a selected orientation relative to the coil 12 such that, when the coil is installed or wound onto the ferromagnetic rod 64, a minimum length of lead wire 75 is needed to connect the coil to the capacitor. This orientation of the recess 68 and the capacitor 16 also provides a compact tunable configuration that increases commonality of the miniature marker assembly 10, which makes mass production of tuned marker assemblies 10 more efficient and economical.

In one embodiment, a spacer or coating is provided within the recess 68 between the endcap 66 and the capacitor 16. The spacer or coating can help avoid electrical shorts with the capacitor 16 and can provide a surface with different bonding characteristics to hold the capacitor in place.

The small physical size and fragility of the signal element 18 are such that complete assembly of the tuned signal element can be difficult. The small capacitors 16, especially the standard 0603, 0504, and 0402 size capacitors, can be dramatically affected during the process of soldering the lead wires 75 to the terminals 73. These small capacitors 16 have such high ratios of contact surface area to total volume that they can inadvertently adhere to a soldering tip during the assembly process, which can result in a failed joint or a damaged capacitor.

Mounting the capacitor 16 in the recess 68 helps alleviate the manufacturing difficulties, because the endcap 66 holds the capacitor in place with the proper, known, and consistent orientation with respect to the coil 12 and lead wires 75. When the capacitor 16 is centered in the recess 68, the capacitor is captured between the side portions of the endcap 66. The side portions work with the adhesive to provide a protective structural support for the capacitor 16. With this method, a simple axial load can be applied to retain the capacitor 16 within the recess 68 during application and curing of an adhesive. Once the capacitor 16 is structurally secured in the recessed endcap 66, the coil lead wires 75 may be readily soldered to the capacitor terminals 73.

Figures 12, 13:
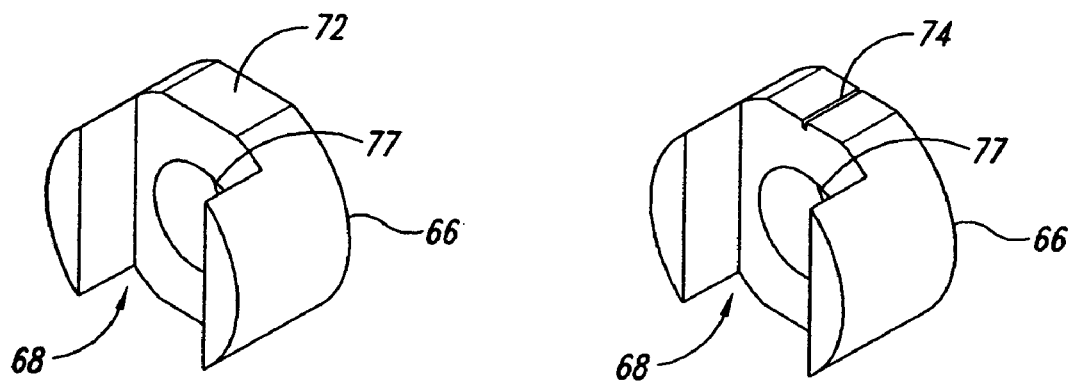
FIG. 12 is an enlarged isometric view of an endcap of an alternate embodiment of the marker assembly of FIG. 10.
FIG. 13 is an enlarged isometric view of an endcap of an alternate embodiment of the marker assembly of FIG. 10.

As seen in FIG. 12, in one alternate embodiment, a flat section 72 is formed on the side of the endcap 66 adjacent to the recess 68 to accommodate the coil lead wires 75 (FIG. 11). The flat sections 72 help prevent the coil 12's fragile lead wires 75 from being snagged or damaged during the process of encasing the completed signal element 18 into the encapsulation member 20 (FIG. 1). In this alternate embodiment, the endcap 66 is also provided with an aperture 77 shaped and sized to receive the core's ferromagnetic rod 64 (FIG. 10) so that the endcap may be axially adjusted on the ferromagnetic rod to tune the signal element 18. The other endcap 62 (FIG. 10) without the recess can also be axially adjustable on the ferromagnetic rod 64 to tune the signal element 18 as discussed above.

In an alternate configuration, the connections between the coil 12 and the capacitor 16 are covered or sealed with an adhesive or epoxy prior to the encapsulation process. Sealing the connections helps prevent damage during the encapsulation process and helps prevent corrosion of the signal element in cases where the marker encapsulation is damaged during or prior to implantation. The connection between the coil 12 and capacitor 16 is an area of the signal element where the small diameter wire is not protected by a coating of insulation.

As best seen in FIG. 13, another embodiment of the recessed endcap 66 includes a groove 74 formed in the outer surface of the endcap adjacent to the recess 68. The groove 74 is sized and positioned to accommodate the coil 12's lead wires 75 (FIG. 11). The groove 74 helps to protect the lead wires 75 from being damaged during the encapsulation process of the signal element 18 to form a hermetically sealed, miniature resonating marker assembly 10.

Figure 14:
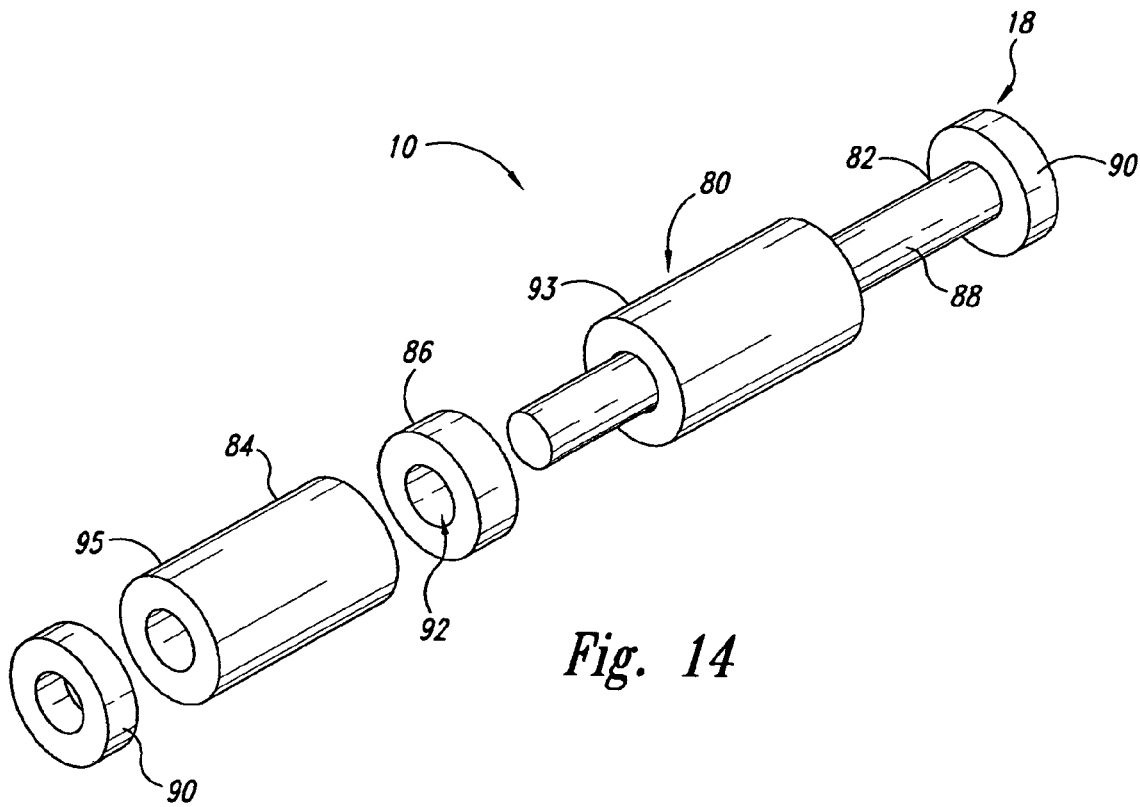
FIG. 14 is an isometric view of a miniature resonating marker assembly in accordance with an alternate embodiment of the present invention, an annular-shaped capacitor being shown positioned on the core between two segments of the wire coil.

FIG. 14 is a cross-sectional view of a miniature resonating marker assembly 10 of an alternate embodiment In this alternate embodiment, the marker assembly 10 includes a signal element 80 having a ferromagnetic core 82, a wire coil 84, and an annular-shaped capacitor 86 to form the signal element that resonates at a selected frequency upon external excitation. The ferromagnetic core 82 in the illustrated embodiment includes a central ferromagnetic rod 88 and a pair of enlarged endcaps 90 secured to the ends of the ferromagnetic rod. The endcaps 90 are disk-shaped members with a central aperture that receives the ferromagnetic rod 88 so the endcaps can be axially adjusted to tune the signal element 80 before the endcaps are fixed in place. In an alternate embodiment, one or both of the endcaps 90 can be integrally connected to the ferromagnetic rod 88.

The annular-shaped capacitor 86 in this alternate embodiment has a similar disk shape and outer diameter as that of the endcaps 90. A central aperture 92 extends through the capacitor 86, and the ferromagnetic rod 88 extends through the capacitor's central aperture. Accordingly, the capacitor 86 is positioned generally in the middle of the signal element 80 between the endcaps 90.

The coil 84 is wound in two segments onto the ferromagnetic rod 88 between the endcaps 90 and the capacitor 86. Accordingly, one coil segment 93 is wound around the ferromagnetic rod 88 between one endcap 90 and the capacitor 86, and a second coil segment 95 is wound around the ferromagnetic rod between the other endcap and the other side of the capacitor. In one embodiment, the two coil segments 93 and 95 are formed by one continuous wire. In an alternate embodiment, the coil segments 93 and 95 may be formed by separate wires interconnected to provide the electrical continuity of the coil 84.

The signal element 80 of this marker assembly 10 is tuned in one embodiment by axially adjusting the position of one or both of the endcaps 90 relative to the ferromagnetic rod 88 and the coil 84 until the signal element is tuned to resonate at the selected frequency. Once the signal element 80 is tuned and the endcaps 90 are secured in position on the ferromagnetic rod 88, the signal element can be encapsulated to provide the inert resonating marker assembly 10.

Figure 15:
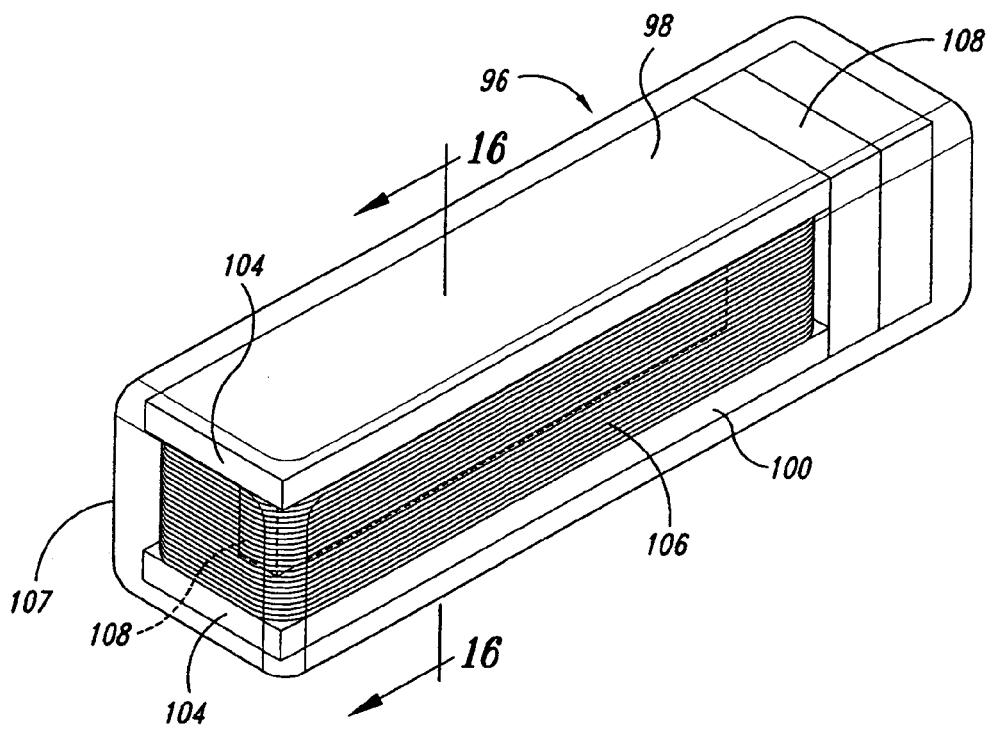
FIG. 15 is an isometric view of a miniature resonating marker assembly in accordance with an alternate embodiment, wherein the ferromagnetic core has an I-beam cross-sectional shape.
Figure 16:
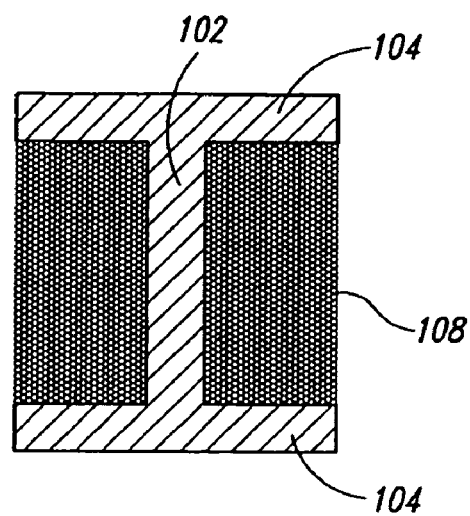
FIG. 16 is an enlarged cross-sectional view of the marker assembly taken substantially along line 16-16 of FIG. 15.

FIG. 15 is an isometric view showing an alternate embodiment of a miniature resonating marker assembly 96. FIG. 16 is a cross-sectional view of the marker assembly 96 of FIG. 15. The marker assembly 96 includes a ferromagnetic core 100 with an I-beam shaped cross-section. The core 100 has an elongated web 102 extending between a pair of ferromagnetic flanges 104 that act as endcaps. In this embodiment, the flanges 104 and the web 102 are integrally connected. In alternate embodiments, the I-beam configuration can be formed by separate flanges 104 adhered or otherwise suitably attached to the web 102.

The marker assembly 96 also includes an elongated coil 106 tightly wound around the web 102 between the flanges 104. The I-beam configuration of the core 100 allows each winding of the elongated coil 106 to cover more of the core 100 than the previously described marker configurations, thereby allowing for more inductance with less wire. In one embodiment, the web 102 has a shorter axial length than the flanges 104, such that the end portions of the web are recessed. The coil 106 is wound around the recessed web 102 so the coil does not extend beyond the ends of the flanges 104 to increase the length of the marker assembly 96. A capacitor 108 (FIG. 15) is securely mounted to one end of the ferromagnetic core 100 and is operatively connected to the lead wires from the coil 106. The capacitor 108 is, thus, substantially coaxially aligned with the core 100 and the coil 106 so as to provide an elongated signal element 98 insertable into an encapsulating member 107 and sealed to provide the inert, miniature marker assembly 96.

Figure 17:
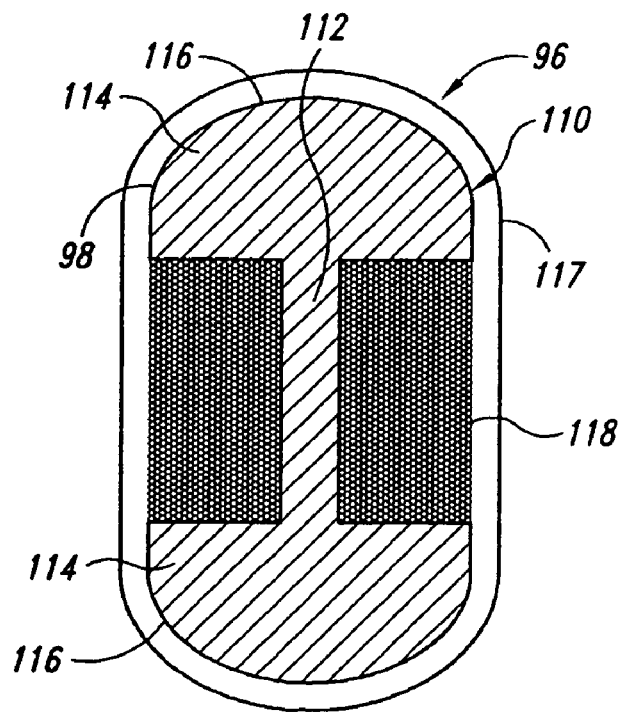
FIG. 17 is an enlarged cross-sectional view of an alternate embodiment of the marker assembly of FIG. 15.

FIG. 17 is a cross-sectional view of an alternate embodiment of the marker assembly 96. This alternate marker assembly 96 includes an elongated ferromagnetic core 110 with a central web 112 and a pair of endcaps 114 connected to the web. Each endcap 114 has a curved or arcuate upper surface 116 that provides for a smooth, rounded signal element 98 that can be easily and quickly inserted into a generally cylindrical encapsulation member 117. Accordingly, the shape of the signal element 98 helps avoid misalignment or binding with the encapsulation member 117 during the installation process in the small encapsulation member. While the illustrated embodiments show geometric configurations of I-beam shapes with flat or curved flanges, other geometric configurations can be used to form the endcaps while providing a suitable area to retain the windings of the coil 118 therebetween.

Figure 18:
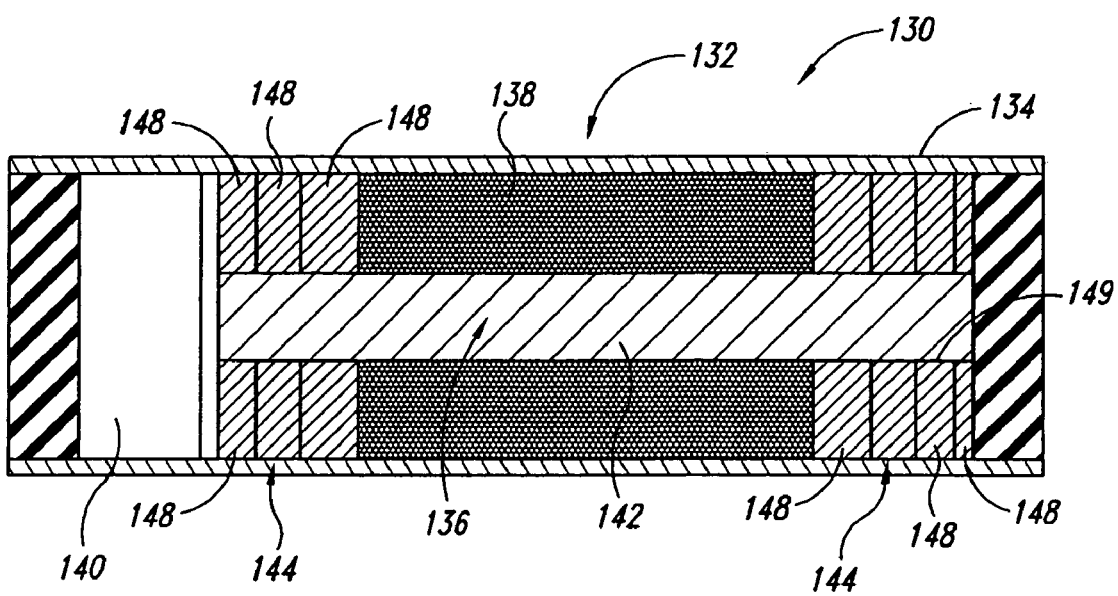
FIG. 18 is a cross-sectional view of a miniature resonating marker assembly in accordance with an alternate embodiment with a plurality of modular endcaps positioned on a central portion of a ferromagnetic core.

FIG. 18 is a cross-sectional view of a modular miniature marker assembly 130 of an alternate embodiment. The marker assembly 130 includes a tuned signal element 132 encapsulated in an outer, inert encapsulation member 134 sealed at its ends to fully enclose the signal element. The signal element 132 in the illustrated embodiment includes a ferromagnetic core 136, a coil 138 wound about the core in a tight-winding configuration discussed above and shown in FIG. 3. A capacitor 140 is attached to the core 136 and operatively connected to the coil 138. The coil 138 and the capacitor 140 are similar to those described above in the embodiments. The core 136 includes a central ferromagnetic rod 142 that extends axially through the coil 138, and a pair of modular endcaps 144 are mounted on the ferromagnetic rod on opposite sides of the coil 138.

The modular endcaps 144 are made up of a plurality of annular-shaped ferromagnetic disks 148 each with a central aperture 149 that receives the end portion of the ferromagnetic rod 142. If an asymmetric core 136 is desired, the modular endcaps 144 can be easily constructed with a different number of ferromagnetic disks 148 or with disks of different thicknesses, so as to achieve the selected ultimate volume of ferromagnetic material at each end of the ferromagnetic rod 142. Accordingly, the characteristics of the signal element 132 can be selected and/or modified by combining a different number or type of ferromagnetic disks 148 to form the modular endcaps 144.

When a large number of miniature marker assemblies 130 are to be manufactured, the same modular components of the ferromagnetic core 136 can be used in different combinations to achieve the tuned marker assembly. Once the modular endcaps 144 are in place on the ferromagnetic rod 142, the ferromagnetic disks 148 can be adjusted axially relative to the ferromagnetic rod and the coil 138 to actively tune the marker assembly 130 to resonate at the selected frequency. Alternatively, the ferromagnetic rod 142 may be axially moved relative to the coil 132 and the modular endcaps 144 to achieve the necessary inductance to tune the signal element 132. After the signal element 132 is accurately tuned, the modular endcaps 144 and central ferromagnetic rod 142 are fixed in position so the signal element remains accurately tuned. The signal element 132 can then be inserted into the encapsulation member 134 and hermetically sealed.

In an alternate embodiment, the characteristics of the signal element 132 may be controlled by combining a central rod 142 made of one ferromagnetic material, and enlarged endcaps 144 made of another ferromagnetic material. The ferromagnetic material for the rod 142 has a first magnetic permeability and saturates at a high field strength, and the ferromagnetic material for the endcaps 144 has a greater magnetic permeability and saturates at a lower field strength. Accordingly, the ferromagnetic core 136 can have a substantially uniform saturation characteristic throughout the core, thereby minimizing the effects of saturation on the resonating marker assembly 130. As an example, in one embodiment, the endcaps 144 may be made of Fair Rite 78 and the ferromagnetic rod 142 may be manufactured of a power ferromagnetic having less magnetic permeability and a higher saturation level. The ferromagnetic rod 142 made of the power ferromagnetic material allows more windings around the rod to form the coil 138 without saturation of the central ferromagnetic rod.

The windings and the core 136 including endcaps 144 of the signal element 132 makeup the elements of the signal element's inductor. For a first order approximation, the inductance of the signal element 132 is optimized for a given volume when the number of turns is maximized, the enclosed area for each turn is maximized, the length of the coil is minimized, the initial permeability of the core is maximized, and the length/diameter ratio of the core is maximized. Also, for a first order approximation, the quality factor (Q factor) of the signal element 132 is optimized when the inductance is maximized and the resistance of the windings and core 136 is minimized. Typically, the resistance of the windings and core 136 will be nearly equal at the chosen frequency when the inductor has been optimized. Other items that must be addressed when optimizing the Q factor include multiple layer windings, the presence of endcaps 144, and frequency dependent losses including dielectric loss and ferrite loss. Accordingly, the marker assembly 130 is designed to provide a maximum Q factor for the marker assembly at a chosen frequency. The embodiment utilizing endcaps 144 with a material having a different permeability than the ferromagnetic rod 142 can be either modular endcaps as shown in FIG. 18, or can be single, solid endcaps as discussed above and shown, for example, in FIG. 2. Accordingly, the miniature resonating marker assembly 130 can be manufactured with components of different materials and characteristics to provide extreme versatility for desired marker characteristics while allowing the marker assemblies to be manufactured efficiently and cost effectively.

Figure 19:
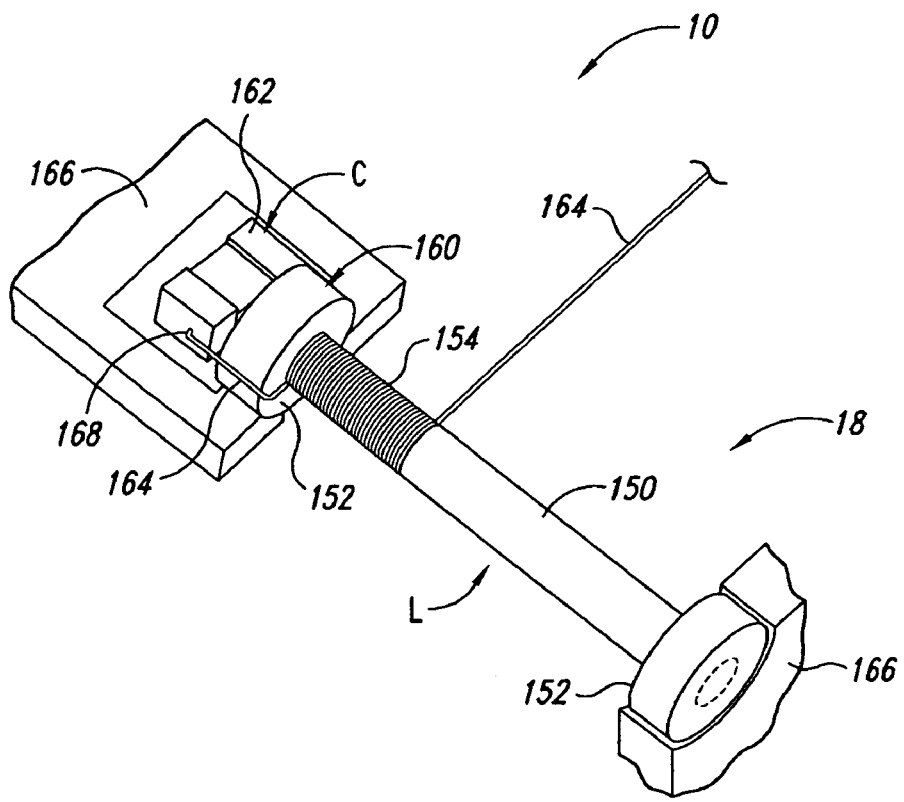
FIG. 19 is an enlarged isometric view illustrating a process of winding a miniature resonating marker assembly in accordance with an embodiment of the present invention.

The process of manufacturing the miniature marker assembly 10 in one embodiment involves actively measuring the marker assembly's inductance during the coil winding process. The process is discussed with reference to FIG. 19. When producing a tuned signal element, which generally consists of an inductor (L) and a capacitor (C) interconnected either in series or in parallel, one significant difficulty is producing an inductor of precise inductance to match imprecise capacitors having tolerances of ±5% or more. Such capacitors are readily available from a number of manufacturers. The manufacturing process of dynamically measuring the inductance of miniature resonating marker coils 154 allows precise control of the inductance of very small inductors, (e.g., with lengths in the range of approximately 1-13 mm, inclusive).

In one embodiment of the manufacturing method, a core 160 with a capacitor 162 affixed thereto is installed in a coil winding machine 166. After the core 160 is positioned in the winding machine 166, a test probe advances forward and makes contact with the capacitor 162 at one test point, such as the capacitor terminal 168. A second test probe is advanced forward to make contact with the other capacitor contact. The capacitor's capacitance is measured and the test probes are retracted. From the capacitance, an empirically derived formula based on the chosen wire size and the core material and other critical inductor parameters are used to identify the inductance value necessary to obtain the desired resonant frequency for the LC series circuit being produced. A single, long strand of wire 164 is connected at one end to the capacitor terminal 168 on the capacitor 162. The coil winding machine 166 is activated to spin the core 160 and capacitor 162 as a unit so as to tightly wind the wire 164 onto the central rod 150 of the ferromagnetic core between the endcaps 152. The windings are controlled to be immediately adjacent to each other so as to minimize the amount of space between windings, as discussed above and shown in FIG. 3.

The individual characteristics of the capacitor 162, the ferromagnetic core 160, and the wire 164 are generally known, so the approximate number of windings needed in the coil 154 can be calculated to approximately achieve the desired inductance needed to tune the signal element. The coil winding machine 166 is used to wind the coil 154 with the initially calculated number of windings. In one embodiment, the coil 154 is wound about the core 160 with a selected number of turns calculated with the empirically derived formula to achieve an inductance value slightly less than necessary to obtain the desired LC series circuit resonant frequency.

After the calculated number of windings are wound onto the core 160, a test probe advances forward making contact with one of the capacitor terminals 168 to which the wire is connected, and another test probe is advanced to make contact with the other end of the wire 164 at the wire takeoff spool (not shown) on the coil winding machine 166. The inductance is dynamically measured and compared to the actual inductance required to obtain the desired resonant frequency of the LC series circuit. The difference between the actual inductance and the target inductance is used to calculate the additional number of windings necessary to add to the coil 154 to accurately achieve the target inductance within a very small margin of error during the manufacturing process. The calculated number of additional windings are added to the coil 154 to achieve the target inductance.

In one embodiment, the actual inductance is measured again after the additional windings are added to the coil 154 to confirm that the actual inductance matches the target inductance within a selected margin of error, as an example, in the range of approximately ±0.2% of the target inductance. The dynamic inductance measurement process can be iteratively used as many times as needed to achieve the inductance needed to obtain the fine-tuned LC series circuit. In one embodiment, if the measured inductance is within 0.5% of the required tuned circuit inductance, the additional windings are added one at a time, with a dynamic inductance measurement taken after each winding is added until the measured inductance matches the required tuned circuit inductance within the resolution of the inductance measuring device.

In one embodiment wherein the coil 154 is wound onto a dumbbell-shaped ferromagnetic core 160, an initial manual process begins with a start turn termination. A small bead of adhesive (e.g., UV-spot-curing type or the like) is used to secure the end of the wire 164 to the ferromagnetic core 160 immediately adjacent to the winding area on the circumference of one of the endcaps 152. The adhesive also serves as a strain relief for the eventual termination to the capacitor terminal 168. The exposed length of wire 164 is twisted back on itself and tinned to provide one of the electrical connections for the dynamic inductance measurement. Following the winding of the first iteration of windings, a service loop is drawn from the wire spool from a location between the spool and the input to a tensioner device. The length of the service loop is determined by the empirically derived formula. As with the start turn termination, the end of the uncut service loop is twisted back on itself and tinned. This provides a second electrical connection for the dynamic inductance measurement.

In the illustrated embodiment, the method of dynamic tuning of the LC series circuit for the resonating marker assembly 10 is used for automated manufacturing of the miniature resonating marker assemblies tuned within a tolerance of approximately ±0.5% of the target resonant frequency. Such highly accurate tuning of the resonating marker assembly 10 allows for extremely accurate manufacturing of relatively large volumes of the miniature resonating marker assemblies in a very efficient and cost-effective manner. In addition, large quantities of miniature resonating marker assemblies 10 having different resonating frequencies can be manufactured efficiently and cost effectively.

Although specific embodiments of, and examples for, the present invention are described herein for illustrative purposes, various equivalent modifications can be made without departing from the spirit and scope of the invention, as will be recognized by those skilled in the relevant art. The teachings provided herein of the present invention can be applied to resonating marker assemblies, not necessarily the exemplary implantable resonating marker assemblies generally described above.

These and other changes can be made to the invention in light of the above-detailed description. In general, in the following claims, the terms used should not be construed to limit the invention to the specific embodiments disclosed in the specification and the claims, but should be construed to include all miniature resonating marker assemblies that operate in accordance with the claims. Accordingly, the invention is not limited by the disclosure, but instead its scope is to be determined entirely by the following claims.

We claim:

1. A method of actively tuning a resonating marker assembly to have a selected resonant frequency value, comprising:
   winding an elongated wire around a central portion of a ferromagnetic core intermediate a pair of ferromagnetic endcaps of the core to form a coil with a plurality of windings, the coil and core forming a combination with a first inductance value;
   measuring the first inductance value of the combination;
   comparing the first inductance to the selected inductance value; and
   adjusting the amount of wire forming the coil after comparing the first inductance value to the selected inductance value by adding or removing one or more turns from the coil until the inductance value of the combination is substantially equal to the selected inductance value.

2. A method of tuning a miniature resonating marker assembly to a selected resonant frequency, comprising:
   placing a ferromagnetic core within a wire coil having a plurality of windings to form an inductor;
   connecting lead wires of the inductor to a capacitor, the capacitor being adjacent to the core to form a miniature signal element;
   exciting the marker assembly at a known frequency; and
   measuring the marker signal intensity or signal phase at the frequency of interest; and adjusting the core axially relative to the windings to adjust the actual inductance until the resonant frequency of the marker matches the desired frequency.

3. A method of tuning a miniature resonating marker assembly to a selected resonant frequency where the impedance of the inductor and capacitor are matched at a selected resonant frequency, comprising:
   placing a core within a wire coil having a plurality of windings;
   connecting lead wires of the inductor to a capacitor with the known capacitance, the capacitor being adjacent to the core to form a miniature signal element;
   measuring the actual resonant frequency of the signal element;
   comparing the actual resonant frequency of the signal element to the selected resonant frequency; and
   adjusting the core axially relative to the winding to adjust the actual resonant frequency until the actual resonant frequency is substantially equal to the selected resonant frequency.

4. The method of claim 3, further comprising fixing the core to the winding to prevent axial movement therebetween after the actual resonant frequency is substantially equal to the selected resonant frequency.

5. The method of claim 3, further comprising winding the coil onto a sleeve with an interior area, and placing the core within the wire coil including placing the core within the interior area of the sleeve.

6. The method of claim 3, further comprising encapsulating the core, the coil, and the capacitor in an inert encapsulation member, and sealing the encapsulation member to hermetically contain the tuned marker assembly.

7. The method of claim 3 wherein the core includes a central portion within the coil and a pair of endcaps, and further comprising positioning an endcap on an end portion of the core's central portion adjacent to the coil, and adjusting the core axially including moving one of the endcaps axially on the central portion relative to the coil.

8. The method of claim 7, further comprising securing the endcap on the core's central portion in a fixed location after the resonant frequency is substantially equal to the selected resonant frequency.

9. The method of claim 3, further comprising forming the wire coil from a plurality of turns of a wire with an airbondable coating thereon to adhere each turn to one or more adjacent turns forming a self supporting winding.

10. The method of claim 3, further comprising securing the core in a fixed position relative to the winding with a ferromagnetic-based adhesive when the actual resonant frequency is substantially equal to the selected resonant frequency.

11. A method of making a tuned, miniature resonating marker assembly with a selected inductance, a known capacitance, and a selected resonant frequency comprising:
   placing a wire coil around a ferromagnetic core having a central portion within the coil and a pair of ferromagnetic endcaps attached to the central portion adjacent to the coil;
   connecting a capacitor to lead wires of the wire coil, the capacitor having a known capacitance and being adjacent to the core, the coil, and the capacitor to form an activatable assembly;
   measuring an actual impedance and phase of the activatable assembly;
   comparing an actual resonant frequency to the selected resonant frequency; and
   removing ferromagnetic-material from the core to adjust the actual resonant frequency of the activatable assembly until the actual resonant frequency is substantially equal to the selected resonant frequency.

12. A method of tuning a miniature resonating marker assembly to a selected resonant frequency, comprising:
   placing a ferromagnetic core within a wire coil having a plurality of windings to form an inductor;
   connecting lead wires of the inductor to a capacitor, the capacitor being adjacent to the core to form a miniature signal element;
   exciting the marker assembly at a known frequency;
   measuring the marker signal intensity or signal phase at the frequency of interest; and
   removing ferromagnetic material from the core to adjust the actual inductance of the activatable assembly until the resonant frequency of the marker matches the desired frequency.

* * * * *